United States Patent [19]

Nudelman et al.

[11] 4,236,002
[45] Nov. 25, 1980

[54] CEPHALOSPORIN DERIVATIVES

[75] Inventors: Abraham Nudelman, Rehovot; Abraham Patchornik, Ness-Ziyona, both of Israel

[73] Assignee: Yeda Research & Development Co., Ltd., Rehovot, Israel

[21] Appl. No.: 863,729

[22] Filed: Dec. 23, 1977

[51] Int. Cl.$^3$ .............................................. C07D 501/22
[52] U.S. Cl. ........................................ 544/28; 544/21; 544/30
[58] Field of Search ................................... 544/30, 28

[56] References Cited

U.S. PATENT DOCUMENTS

| | | | |
|---|---|---|---|
| 3,167,549 | 1/1965 | Hoover | 544/30 |
| 3,579,514 | 5/1971 | McGregor | 544/30 |
| 3,701,775 | 10/1972 | Berges et al. | 544/30 |
| 3,705,892 | 12/1972 | Cooper | 544/30 |
| 3,855,213 | 12/1974 | Dunn et al. | 544/30 |
| 3,985,741 | 10/1976 | Crast et al. | 544/30 |
| 4,012,382 | 3/1977 | Bouzard et al. | 544/30 |
| 4,031,083 | 6/1977 | Haviv et al. | 544/30 |

*Primary Examiner*—Paul M. Coughlan, Jr.
*Attorney, Agent, or Firm*—William J. Stein; L. Ruth Hattan; George W. Rauchfuss, Jr.

[57] ABSTRACT

New 7-[4-hydroxy-3-(substituted methyl)phenyl-]acetamido cephalosporin derivatives are prepared which are useful as antibiotics.

7 Claims, No Drawings

CEPHALOSPORIN DERIVATIVES

FIELD OF INVENTION

This invention relates to novel cephalosporin derivatives useful as antibiotics and processes for their preparation.

SUMMARY OF INVENTION

Compounds of Formula 1 are useful as antibiotic agents

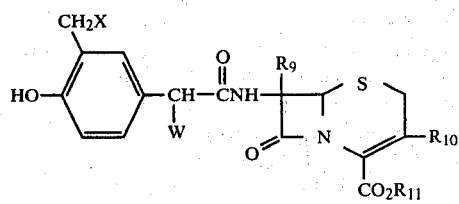

Formula 1 wherein W is hydrogen, hydroxy, —SO$_3$H or —COOR$_1$ wherein R$_1$ is selected from hydrogen, phenyl or 5-indanyl, or a 1 to 4 carbon alkyl group; —NHR$_2$ wherein R$_2$ is hydrogen, tert-butyloxycarbonyl,

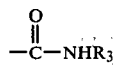

wherein R$_3$ is hydrogen, a lower alkyl group of from 1 to 4 carbon atoms or a phenyl group; X is chloro, bromo, an alkoxy group from 1 to 4 carbon atoms; an R$_4$—S—,

R$_3$SO$_2$— group wherein R$_4$ is a lower alkyl group of from 1 to 4 carbon atoms; azido; cyano; NCNH—; HSO$_3$—; —SCN; —OCN; CH$_3$SO$_2$NH—; isothiourea; substituted isothiourea wherein the substituents are amino, formylamino, guanylamino, a lower alkyl group of from 1 to 4 carbon atoms and concatenated alkylene groups in the form of a series of from 2 to 6 methylene groups; pyridylthio; 1-methyltetrazol-5-ylthio; 1,3,4-thiadiazol-2-ylthio; 1,3,4-triazol-2-ylthio; —SH; SSO$_3$H; F$_3$CS—;

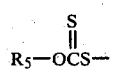

wherein R$_5$ is lower alkyl of from 1 to 4 carbon atoms;

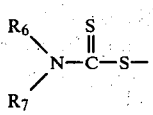

wherein R$_6$ and R$_7$ separately are hydrogen, a lower alkyl group of from 1 to 4 carbon atoms; when taken together R$_6$ and R$_7$ may form a concatenated chain of from 4 to 7 methylene groups, a concatenated chain of from 5 to 7 methylene groups wherein one of these methylene groups is replaced by an oxygen atom or an R$_8$—N group wherein R$_8$ is a lower alkyl group of from 1 to 4 carbon atoms; R$_9$ is hydrogen or methoxy; R$_{10}$ is selected from methyl, acetyloxymethyl, chloro, bromo, methoxy, 1-methyltetrazol-5-ylthiomethyl, 5-methyl-1,3,4-thiadiazol-2-ylthiomethyl, 1,3,4-triazol-2-ylthiomethyl, 1,3,4-thiadiazol-2-ylthiomethyl, tetrazol-5-ylthiomethyl, 1,3,4-oxadiazol-2-ylthiomethyl, 5-methyl-1,3,4-oxadiazol-2-ylthiomethyl, 5-methyl-1,3,4-triazol-2-ylthiomethyl, 1,2,3-triazol-5-ylthiomethyl as represented by the following respective formula

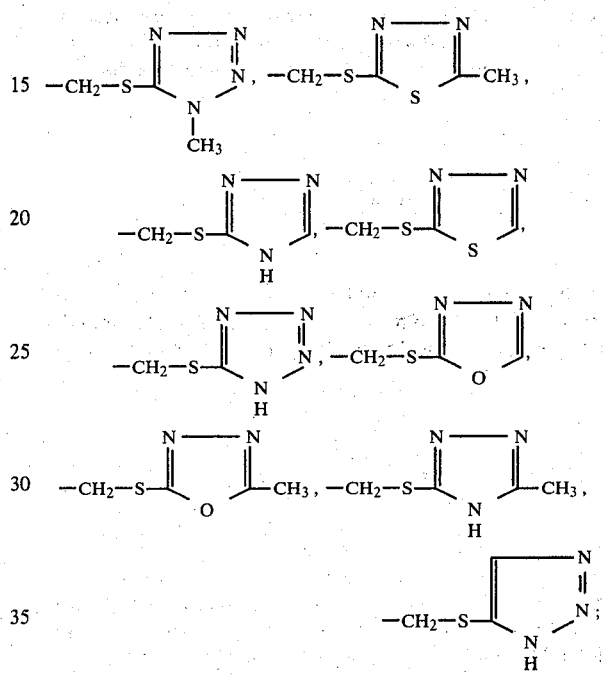

R$_{11}$ is hydrogen, a straight or branched lower alkyl group of from 1 to 4 carbon atoms, a straight or branched alkanoyloxymethyl group in which the alkanoyl moiety has from 1 to 4 carbon atoms, an alkanoylaminomethyl group in which the alkanoyl moiety is straight or branched and has from 1 to 4 carbon atoms and the amine nitrogen may be substituted with a straight or branched lower alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched lower alkyl group of from 1 to 4 carbon atoms, p-(alkanoyloxy)benzyl group in which the alkanoyl moiety has from 2 to 15 carbon atoms and the amino nitrogen may be mono- or di-substituted with a straight or branched lower alkyl group having from 1 to 4 carbon atoms; and pharmaceutically acceptable salts thereof.

DETAILED DESCRIPTION OF INVENTION

In Formula 1 the substituent group as represented by R$_{11}$ in addition to being hydrogen may also be alkanoyloxymethyl as represented by the structure

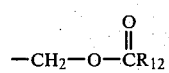

wherein R$_{12}$ is selected from a straight or branched alkyl group of from 1 to 4 carbon atoms; R$_{11}$ is an alkanoylaminomethyl or alkoxycarbonylaminomethyl as represented by the structure

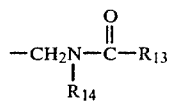

wherein $R_{13}$ represents a straight or branched alkyl group of from 1 to 4 carbon atoms or a straight or branched alkoxy group of from 1 to 4 carbon atoms, and $R_{14}$ is selected from hydrogen and a straight or branched alkyl group of from 1 to 4 carbon atoms; $R_{11}$ is a p-(alkanoyloxy)benzyl group as represented by the structure

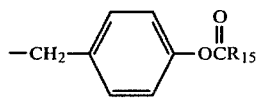

wherein $R_{15}$ is a straight or branched alkyl group of from 1 to 4 carbon atoms; and $R_{11}$ is an aminoalkanoyloxymethyl group as represented by the structure

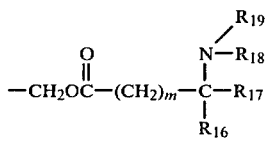

wherein m is 0 to 5, each of $R_{16}$ and $R_{17}$ is selected from hydrogen or a straight or branched alkyl group of from 1 to 4 carbon atoms, and each of $R_{18}$ and $R_{19}$ is selected from hydrogen or a straight or branched alkyl group of from 1 to 4 carbon atoms.

Illustrative examples of straight or branched alkyl groups of from 1 to 4 carbon atoms which $R_3$ to $R_8$ and $R_{12}$ to $R_{19}$ inclusive may represent are methyl, ethyl, n-propyl, iso-propyl, n-butyl, sec-butyl and tert-butyl. X may represent a methoxy, an ethoxy, a propoxy or a tert-butoxy group.

In Formula 1, the substituent group $R_{10}$ may represent in addition to methyl, acetyloxymethyl, chloro, bromo, or methoxy, a heterocyclic thiomethyl group selected from 1,3,4-thiadiazol-2-ylthiomethyl, 5-methyl-1,3,4-thiadiazol-2-ylthiomethyl, tetrazol-5-ylthiomethyl, 1-methyltetrazol-5-ylthiomethyl, 1,3,4-oxadiazol-2-ylthiomethyl, 5-methyl-1,3,4-oxadiazol-2-ylthiomethyl, 1,2,3-triazol-5-ylthiomethyl or 1-methyl-1,2,3-triazol-5-ylthiomethyl, as represented by the following respective structures:

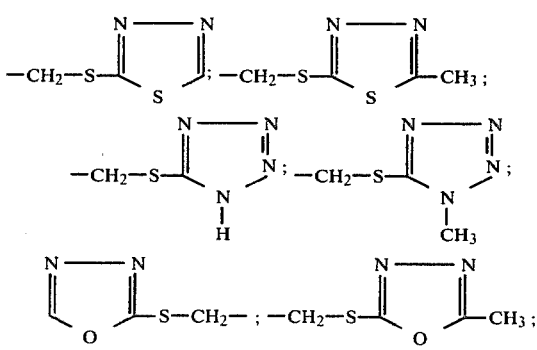

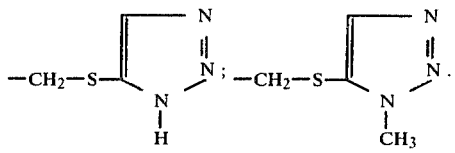

In Formula 1, $R_9$ is hydrogen or methoxy. It is apparent that the group $R_9$ may be either cis or trans to the hydrogen atom at the 6-position of the cephalosporin derivative. Those compounds in which the $R_9$ group is cis to the 6-position hydrogen are preferred.

The non-toxic pharmaceutically acceptable inorganic acid addition salts of compounds of this invention such as mineral acid addition salts, for example, hydrogen chloride, hydrogen bromide, hydrogen iodide, sulfates, sulfamate, phosphate, and organic acid addition salts, for example, maleate, acetate, citrate, oxalate, succinate, benzoate, tartrate, fumarate, malate, mandelate, ascorbate and trifluoroacetate are also included within the scope of this invention.

Also within the scope of this invention are the non-toxic pharmaceutically acceptable salts of the compounds of Formula 1 of this invention wherein W represents $-CO_2R_1$ ($R_1=H$), or $SO_3H$ and compounds wherein $R_{11}$ represents hydrogen. Illustrative non-toxic pharmaceutically acceptable salts of these acid derivatives include the alkali metal and alkaline earth metal salts such as the sodium, potassium, calcium or magnesium salts and the primary, secondary or tertiary amine salts, for example, cyclohexylamine, diethylamine and pyridine.

The compounds of this invention may be administered in a manner similar to that of many well-known cephalosporin compounds, for example, cephalexin, cephalothin, or cephaloglycine. They may be administered alone or in the form of pharmaceutical preparations either orally or parenterally and topically to warm blooded animals, that is, birds and mammals, for example, cats, dogs, cows, sheep and horses, and humans. For oral administration, the compounds may be administered in the form of tablets, capsules or pills or in the form of elixirs or suspensions. For parenteral administration, they may be used in the form of a sterile aqueous solution which may contain other solutes, for example, enough saline or glucose to make the solution isotonic. For topical administration, the compounds may be incorporated in creams or ointments.

Illustrative examples of bacteria against which the compounds of this invention are active are *Staphylococcus aureus, Salmonella schottmuelleri, Klebsiella pneumoniae, Diplococcus penumoniae,* and *Streptococcus pyogenes.*

An illustrative example of a cephalosporin derivative of this invention is 7-[[amino[4-hydroxy-3-(methoxymethyl)phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid.

The preferred embodiments of this invention are:

A. Compounds wherein W represents hydrogen, hydroxy, amino, $SO_3H$ and $COOR_1$ wherein $R_1$ represents hydrogen in that such substitution results in compounds having broader spectrum of activity and/or improved oral activity for example, compounds wherein 1. W represents hydroxy are more resistant to β-lactamase;
2. W represents SO₃H or COOR₁ wherein R₁ represents hydrogen have broader gram negative spectrum;
3. W represents NH₂ have improved oral activity;

B. Compounds wherein R₉ represents methoxy are of particular interest in that such compounds demonstrate antibacterial activity against cephalosporinase producing gram negative organisms.

C. Compounds wherein R₁₀ represents methyl, chloro, bromo, methoxy, 2-methyl-1,3,4-thiadiazol-5-ylthiomethyl or 1-methyltetrazol-5-ylthiomethyl.

The compounds of general Formula 1 may be prepared by coupling an amine compound of Formula 2

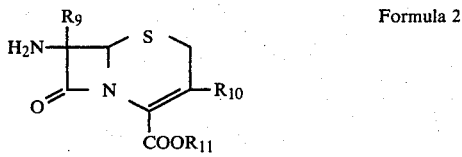

Formula 2 with an acid of Formula 3 or a functional equivalent thereof

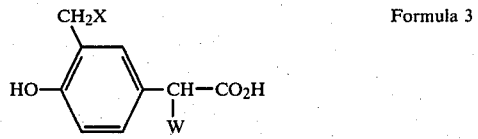

Formula 3 wherein R₉, R₁₀ and R₁₁ have the meanings defined in Formula 1, X is other than —SO₃H and W is as defined in Formula 1 with the proviso that —NH₂ and —OH must be protected or —CO₂H and —SO₃H may be protected, with a further proviso that when X is chlorine or bromine, then R₂ is other than a tert-butyloxycarbonyl group. Optionally, the coupling reaction may be run in the presence of N-ethoxy-2-ethoxy-1,2-dihydroquinoline provided that W is as defined in claim 1 with the proviso that amino, hydroxyl, carboxyl and sulfo groups must be protected and R₁₁ is other than hydrogen or a cation. Furthermore, the coupling reaction may optionally be run in the presence of a dehydrating agent, for example, a carbodiimide.

Illustrative examples of protecting groups which are used for the specific reactive groups such as —NH₂, —OH, —CO₂H and —SO₃H are as follows. For an amine group the protecting group may be an acid salt such as the hydrochloride or the hydrobromide, an alkoxycarbonyl group, for example, tert-butoxycarbonyl; an alkanoyl group, for example, an acetyl group; or a benzoyl group. The hydroxyl group may be protected with a trimethylsilyl group. Acid groups such as —CO₂H and —SO₃H may be protected with an alkyl group such as methyl, ethyl, tert-butyl or with an alkanoyloxymethyl group such as privaloyloxymethyl.

Functional equivalents of the acids as represented by Formula 3 include the acid halides, for example, the acid chloride, acid anhydrides, including mixed anhydrides with, for example, alkylphosphoric acids, lower aliphatic monoesters of carbonic acid, or alkyl or aryl sulfonic acids. Additionally, the acid azide or an active ester or thioester, for example, with p-nitrophenol, 2,4-dinitrophenol, or thioacetic acid, may be used.

The coupling reaction is generally carried out in the presence of a solvent. Suitable solvents include, for example, benzene, ethyl acetate, acetone, dioxane, acetonitrile, chloroform, ethylene chloride, tetrahydrofuran, dimethylformamide, water and mixtures thereof.

The coupling reaction may be carried out in the presence of a base such as sodium bicarbonate, triethylamine or N,N-dimethylaniline.

The temperature of the coupling reaction may vary from −10° to 100° C., and the reaction time may vary from about ½ hour to 16 hours. The products are isolated by conventional methods.

Illustrative examples of coupling reactions useful in obtaining compounds of Formula 1 are as follows.

The general method described by Spencer, et. al., *J. Med. Chem.*, 9, 746 (1966) may be used to form Formula 1 compounds. An acid of Formula 3 is first converted to a functional equivalent (mixed anhydride) by reacting the acid with an alkylchloroformate in the presence of an acid acceptor (for example, triethylamine) in a solvent at about −10° C. The amine with which the acid is to be coupled to form compounds as represented by Formula 1 is added and the temperatures increased from about −10° C. to about room temperature (about 20° C.). The reaction is completed and the coupled product is recovered by conventional methods.

Another illustrative method which may be used to prepare compounds of Formula 1 involves the coupling of 1 equivalent of an acid as represented by compounds of Formula 3 with 1 equivalent of an amine as represented by compounds of Formula 2 in the presence of about 1 to 2 equivalents of a carbodiimide according to the general procedure described in U.S. Pat. No. 3,252,973.

Optionally, the method of Belleau may be used to form compounds of Formula 1. Acids as represented by compounds of Formula 3 may be coupled with compounds as represented by Formula 2 in the presence of N-ethoxycarbonyl-2-ethoxy-1,2-dihydroquinoline (EEDQ), provided that W is other than —NH₂, —OH, —COOH or —SO₃H and R₁₁ is other than hydrogen. Using the general method of Belleau, et al., *J. Am. Chem. Soc.*, 90, 1651 (1968), equivalent amounts of the acid, the amine and EEDQ are stirred in a suitable solvent for 2 to 12 hours at a temperature of about 20° to about 70° C. The coupled product is recovered by conventional techniques.

Illustratively, a compound as represented by Formula 3 wherein W is —COOH or —SO₃H may be coupled to a compound as represented by Formula 2 using the general procedure as described in U.S. Pat. No. 3,282,926. The monoacid chloride of a compound of Formula 3 is reacted with a 7-amino derivative of compounds of Formula 2 in the presence of an acid acceptor at a temperature of about 0° C. to about 30° C. for from 30 minutes to 2 hours to give the coupled compounds which is recovered by conventional techniques.

Compounds of Formula 1 wherein X is other than bromine, chlorine, an R₄SO— or an R₄SO₂— group, W is as defined for Formula 1 with the proviso that R₂ is other than tert-butyloxycarbonyl group and R₉, R₁₀ and R₁₁ are as defined in Formula 1 may be prepared by reacting 1 equivalent of a compound of Formula 1 wherein X is chlorine or bromine with 1 to 10 equivalents of a nucleophilic reagent in a suitable solvent such as tetrahydrofuran, tetrahydrofuran-water, dimethylformamide, acetone, chlorinated aliphatic hydrocarbons such as methylene chloride, chloroform or ethylene dichloride or dimethylformamide at a temperature of from 10° C. to about 100° C. for from 0.5 hour to 48 hours. The nucleophilic reagents may be selected from sodium azide, silver cyanide, methanol, sodium methoxide, sodium methylthiolate, calcium cyanamide, sodium bisulfite, ammonium thiocyanate, silver cyanate, sodium methanesulfonamide, thiourea, thiosemicarbazide, guanylthiourea, ethylene thiourea, formylthiosemicarbazide, silver trifluoromethylthiolate, sodium thiosulfite, 2,3 or 4-mercaptopyridine, sodium sulfide, 1-methyltetrazol-5-ylthiol, 1,3,4-thiadiazol-5-ylthiol, 1,3,4-triazol-2-ylthio, potassium ethylxanthate, $H_2N-C(S)SNH_4$,

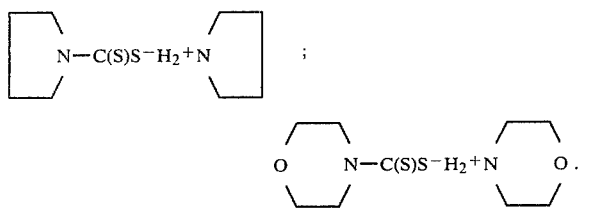

Compounds of Formula 3 are prepared by methods described herein.

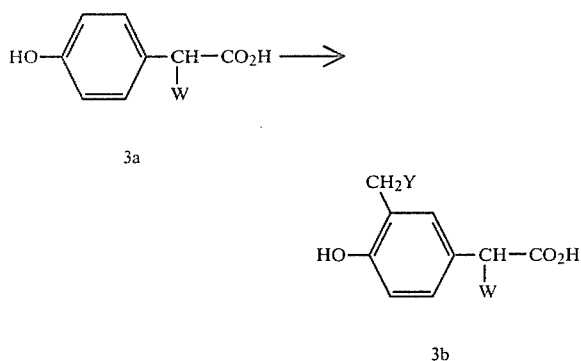

Compounds of Formula 3a wherein W is hydrogen, hydroxyl, amino, carboxyl, optionally substituted with a 1 to 4 carbon alkyl group, a phenyl group or an indanyl group, sulfo or ureido which may optionally be mono-substituted with an alkyl group of from 1 to 4 carbon atoms or a phenyl group are commercially available, are described in the literature or are described herein, and may be reacted with an equivalent amount of formaldehyde in a reaction medium such as hydrochloric acid, hydrobromic acid, acetic acid, phosphoric acid or sulfuric acid, optionally in the presence of a Lewis acid catalyst such as $AlCl_3$, $TiCl_4$ or $SnCl_4$ at $-10°$ C. to $100°$ C. for from 30 minutes to 10 hours. Gaseous hydrogen chloride or hydrogen bromide is passed through the reaction medium. A compound of Formula 3b wherein Y is chlorine or bromine is obtained.

Compounds of Formula 3 wherein X is other than $R_4SO-$, $R_4SO_2-$, chlorine or bromine may be prepared by the nucleophilic displacement of a halogen atom from 1 equivalent of a compound of Formula 3b by means of 1 to 10 equivalents of a nucleophile, MZ, as shown below.

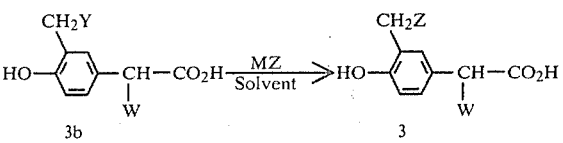

W is as defined for Formula 1 with the proviso that $R_2$ is other than a tert-butyloxycarbonyl group. Y represents chlorine or bromine.

The nucleophiles, represented by MZ, are commercially available or may be prepared by standard procedures known in the art. Illustratively, compounds represented by MZ may be the following: sodium azide, silver cyanide, methanol, sodium methoxide, sodium methylthiolate, calcium cyanamide, sodium sulfite, potassium bisulfite, ammonium thiocyanate, silver cyanate, sodium methanesulfonamide, thiourea, thiosemicarbazide, guanylthiourea, ethylene thiourea, formylthiosemicarbazide, silver trifluoromethylthiolate, sodium thiosulfite, 2,3 or 4-mercaptopyridine, sodium sulfide, 1-methyltetrazol-5-ylthiol, 1,3,4-thiadiazol-5-ylthio, 1,3,4-triazol-2-ylthio, potassium ethylxanthate, $H_2N-C(S)SNH_4$,

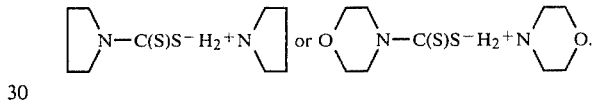

The nucleophilic discplacement reaction is conducted in a suitable solvent such as water, methanol, ethanol, isopropanol, dimethylformamide, dimethylsulfoxide, acetonitrile, acetone and mixtures thereof, at temperatures from $0°$ C. to $100°$ C. for from 0.5 hour to 30 hours.

Compounds of Formula 3 where X is an $R_4SO-$ or an $R_4SO_2-$ group may be prepared by the stepwise sulfur-oxidation of compounds of Formula 3 where X is an $R_4S-$ group. For example, the stepwise sulfur-oxidation may be carried out in a suitable solvent such as water, water-methanol, or water-acetic acid with an equivalent or an excess of oxidizing agent at a temperature of $0°$ to $50°$ C. for from 3 to 15 hours. An equivalent amount of the sulfur-oxidizing agent gives the $R_4SO-$ compound, an excess of the sulfur-oxidizing agent gives the $R_4SO_2-$ compound.

Compounds of Formulas 1 and 3 where $R_2$ is a tert-butyloxycarbonyl group may be prepared from the corresponding compounds of Formulas 1 and 3 where $R_2$ is hydrogen. For example, a compound of Formula 1 or 3 wherein $R_2$ is hydrogen may be reacted with a reagent such as tert-butyloxycarbonylazide, 2-(tert-butyloxycarbonyloxyimino)-2-phenylacetonitrile or di-tert-butyldicarbonate at a temperature of from $10°$ to $60°$ C. for from 2 hours to 20 hours in a suitable solvent for example, water, dioxane, tert-butanol or mixtures thereof and in the presence of a basic material, for example, magnesium oxide, triethylamine or sodium hydroxide; the molar ratio of the compound of Formula 1 or 3 to the reagent is from 1 to 1 to 1 to 2.

The protecting groups, such as tert-butyl, tert-butyloxycarbonyl and acetyloxymethyl may be removed from a compound of Formula 1 by methods well known. For example, a compound of Formula 1 wherein $R_2$ is tert-butyloxycarbonyl and $R_{11}$ is tert-butyl is reacted with trifluoroacetic acid at $-10°$ to $20°$ C. for from 2 to 60 minutes. Removal of the trifluoroacetic acid and neutralization of the residual trifluoroacetate salt gives a compound of Formula 1 where $R_2$ and $R_{11}$ are hydrogen.

Compounds of Formula 2 wherein $R_9$ is hydrogen, $R_{11}$ is hydrogen or a cation and $R_{10}$ is methyl or acetyloxymethyl are commercially available or may be prepared by the methods well-known in the art. The corresponding compounds wherein $R_9$ is methoxy, $R_{10}$ is methyl or acetyloxymethyl and $R_{11}$ is hydrogen may be prepared by the general procedures described in U.S. Pat. No. 3,778,432.

Compounds of Formula 2 wherein $R_{10}$ is defined as chloro, bromo, methoxy may be prepared by the general procedure described in *J. Am. Chem. Soc.*, 96, 4986 (1974) and *J. Med. Chem.*, 18, 403 (1975).

Compounds of Formulas 1 and 2 wherein $R_{11}$ is alkanoyloxymethyl may be prepared by reacting the corresponding acid, $R_{11}$ is hydrogen, in the form of a salt, such as an alkali metal salt or the triethylammonium salt with a compound of the formula:

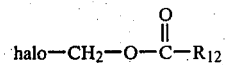

wherein halo is chlorine or bromine, and $R_{12}$ is a straight or branched alkyl group of from 1 to 4 carbon atoms, by the general procedure described in U.S. Pat. No. 3,655,658.

Compounds of Formulas 1 and 2 wherein $R_{11}$ is alkanoylaminomethyl or alkoxycarbonylaminomethyl are prepared by treating the sodium salt of the corresponding acid ($R_{11}$=hydrogen) derivatives of Formulas 1 and 2 in an organic solvent such as dimethylformamide or hexamethylphosphoramide at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of Formulas 1 and 2 wherein $R_{11}$ is p-(alkanoyloxy)benzyl are prepared by adding 2 equivalents of the p-(alkanoyloxy)benzyl alcohol to a suspension of the sodium salt of the corresponding acid derivative, $R_{11}$=hydrogen, of Formulas 1 and 2 and dimethylformamide or hexamethylphosphoramide after which the mixture is cooled to 0° C. 1.2 equivalents of dicyclohexylcarbodiimide and dimethylformamide are added dropwise to the mixture with stirring. The mixture is stirred at 0° C. for ½ to 3 hours and then an additional 2 to 5 hours at room temperature. The formed dicyclohexylurea is removed by filtration. The filtrate is diluted with chloroform, methylene chloride or ethyl acetate, washed with water, dried and evaporated to give the product.

Compounds of Formulas 1 and 2 wherein $R_{11}$ is aminoalkanoyloxymethyl are prepared by mixing a suspension of the sodium salt of the corresponding acid, $R_{11}$=hydrogen, of Formulas 1 and 2 and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethyl acetate or methylene chloride, washed with water, aqueous base, then water. The organic phase is separated and the precipitate isolated by conventional means followed by deprotection of the amine group to give the product.

Compounds represented by Formulas 1 and 2 wherein $R_9$ is hydrogen or methoxy, $R_{10}$ is a heterocyclic thiomethyl group as described in Formula 1 and $R_{11}$ is hydrogen and X is other than chlorine or bromine in compounds of Formula 1 are prepared by dissolving 1 equivalent of an acid, represented by compounds of Formula 1 or 2 wherein $R_9$ is hydrogen or methoxy, $R_{10}$ is acetyloxymethyl, and $R_{11}$ is hydrogen, and X is other than chlorine or bromine in compounds of Formula 1, in the form of a salt, such as the sodium salt, in about 500 to 2000 ml of water at a temperature of from about 30° to about 90° C. under a nitrogen atmosphere, and then adding 1 equivalent of a base, such as, sodium bicarbonate or triethylamine and 1 to 3 equivalents of the appropriate heterocyclic thiol selected from a compound having the following structure:

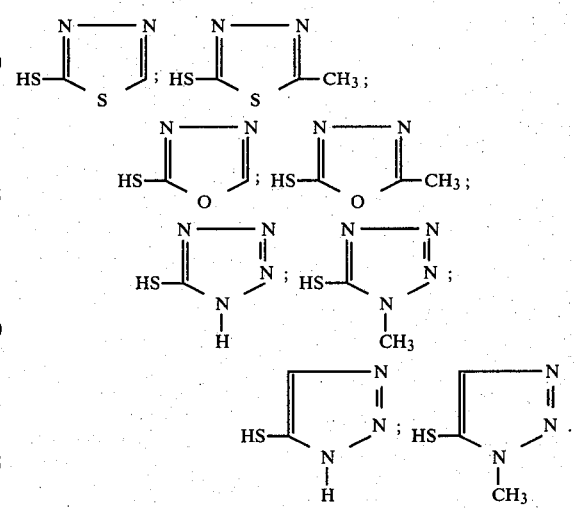

The displacement of the acetyloxy group by the heterocyclic thiol compounds is also realized when compounds of Formula 1, $R_9$ is hydrogen or methoxy, $R_{10}$ is acetyloxymethyl, $R_{11}$ is hydrogen and X is other than chlorine or bromine, are treated with an appropriate heterocyclic thiol according to the general procedure described in *J. Antibiotics*, 23, 131 (1966).

The daily dosage of the active ingredient may range from 1 mg to about 500 mg. The exact amount will vary with the patients' size, age and type of infection.

A typical tablet can have the following composition.

| | |
|---|---|
| 7-[[amino[4-hydroxy-3-(methoxymethyl)-phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid | 50 mg |
| Lactose, USP | 250 mg |
| Cornstarch, USP | 50 mg |
| Cornstarch, USP (as 10% starch paste) | 5 mg |
| Calcium Stearate | 2 mg |

Suitable size tablets can be prepared using a 5/16 inch diameter standard concave punch.

A typical parenteral solution may have the following composition.

7-[[amino[4-hydroxy-3-(methoxymethyl)-phenyl]acetyl]amino]-3-[[(1-methyl-1H-tetrazol-5-yl)thio]methyl]-8-oxo-5-thia- -continued

| | |
|---|---|
| 1-azabicyclo[4.2.0]oct-2-ene-2-carboxylic acid, sodium salt | 1.0 g |
| White beeswax | 1.0 g |
| Peanut oil, to make | 10.0 cc |

Melt wax into a portion of the peanut oil. Add the remainder of the oil. Sterilize the oil-wax mixture at 150° C. with dry heat for 2 hours. Under sterile conditions mix the cephalosporin into the wax-oil mixture and place in a 25 cc ampule previously sterilized and seal ampule. For use, dilute with 10 cc of pure water; each cc contains 50 mg of cephalosporin.

A typical ointment can have the following composition.

| | |
|---|---|
| 7-[[amino[4-hydroxy-3-(methoxymethyl)-phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt | 50 mg/gram of ointment |
| Hydrophilic Base | |
| Cetyl alcohol | 15% |
| White Wax | 1% |
| Sodium Lauryl sulfate | 2% |
| Propylene glycol | 10% |
| Water | 72% |

Add the cephalosporin derivative to a small amount of water and incorporate into the base.

EXAMPLE 1

(−)-α-Amino-3-(chloromethyl)-4-hydroxybenzeneacetic acid hydrochloride

To a solution of (−)-α-amino-4-hydroxybenzeneacetic acid (100 g, 0.6 mole) in a minimum amount of concentrated hydrochloric acid at 35°-40° C. is added 50 ml of aqueous formaldehyde (35-37%) (0.6 mole). The addition of hydrogen chloride gas is begun. After 5-10 minutes, a solid begins to precipitate. Stirring is continued for 30 minutes, and the solid is then collected. The crude product is washed with ether and with acetone. A second crop is obtained from the filtrate after standing at room temperature overnight. Total yield is 102 g (67%) m.p. >300° C., $[\alpha]_D^{18} = -134°$ (c 4.75, CH$_3$OH) NMR (DMSO-D$_6$) ppm (δ) 4.68 (s,2), 4.9 (broad s,1), 6.9-7.6 (superimposed q and s,3).

Anal. calcd for C$_9$H$_{10}$ClNO$_3$ HCl: Cl 28.13 Found 26.44

In like manner and using equivalent amounts of (−)-α-amino(4-hydroxybenzene)acetic acid, ethyl ester hydrochloride in place of (−)-α-amino(4-hydroxybenzene)acetic acid gives (−)-α-amino(3-chloromethyl-4-hydroxybenzene)acetic acid, ethyl ester, hydrochloride.

EXAMPLE 2

(−)-α-Amino-3-(bromomethyl)-4-hydroxybenzeneacetic acid hydrobromide

To a solution of (−)-α-amino-4-hydroxybenzeneacetic acid (0.6 mole) in a minimum amount of concentrated hydrobromic acid at 35°-40° C. is added 50 ml of aqueous formaldehyde (35-37%) (0.6 mole). The addition of hydrogen bromide gas is begun. After 5-10 minutes, a solid begins to precipitate. Stirring is continued for 30 minutes. The title compound is collected and washed with ether and acetone.

EXAMPLE 3

3-Chloromethyl-4-hydroxybenzeneacetic acid

4-Hydroxybenzeneacetic acid, 0.5 mole, is added to concentrated hydrochloric acid, 50 ml, then 0.5 mole of formaldehyde in the form of a 34-38% solution of formalin is added. Hydrogen chloride is bubbled through the reaction mixture for 60 minutes while maintaining the temperature of the reaction mixture at 35° to 45° C. The reaction mixture is poured into water and the title compound is extracted from the solution with ethyl acetate. The ethyl acetate is dried over magnesium sulfate, filtered and removed to give the title compound.

EXAMPLE 4

α-Hydroxy-3-(bromomethyl)-4-hydroxybenzeneacetic acid

About 0.3 mole of α-hydroxy(4-hydroxybenzene)acetic acid is added to about 50 ml of concentrated hydrobromic acid containing about 0.1 mole trioxane. The temperature is maintained between about 35° to about 45° C. while passing hydrogen bromide gas through the reaction mixture. After about 90 minutes, the reaction mixture is poured into cold water and the title compound is extracted with ethyl acetate. After drying the organic extract over magnesium sulfate and filtering to remove the magnesium sulfate, removal of the ethyl acetate gives the title compound.

EXAMPLE 5

α-Carboxy-3-(bromomethyl)-4-hydroxybenzeneacetic acid

About 0.5 mole of 4-hydroxybenzeneacetic acid is dissolved in about 50 ml of anhydrous tetrahydrofuran at −40° C. To this solution is added 3 equivalents of lithium diisopropylamide. The temperature is maintained at about −40° C. for about 15 minutes. Then 1 equivalent of ethyl chloroformate is added and the temperature is raised from about −40° C. to about 20° C. and the reaction mixture stirred for about 60 minutes. The reaction mixture is poured into water and the monoester of α-carboxy-4-hydroxybenzeneacetic acid is recovered from the aqueous solution. Hydrolysis of the half-ester with sodium hydroxide followed by acidification with hydrochloric acid gives α-carboxy-4-hydroxybenzeneacetic acid.

α-Carboxy-4-hydroxybenzeneacetic acid, 0.3 mole, is added to aqueous acetic acid (50%) which contains 0.3 mole of chloromethyl methyl ether and a catalytic amount of zinc chloride. The temperature is maintained between about 35° to 45° C. for about 2 hours while hydrogen chloride gas is bubbled through the solution. The reaction mixture is then added to water and the reaction product is recovered by extraction with methylene chloride. After drying the methylene chloride over magnesium sulfate, the magnesium sulfate is removed by filtration. Removal of the methylene chloride gives the title compound.

EXAMPLE 6

α-sulfo-3-(chloromethyl)-4-hydroxybenzeneacetic acid

Approximately 0.6 mole of 4-hydroxybenzeneacetic acid is added to about 0.9 mole of dioxane-SO$_3$ complex in ethylene chloride maintained at room temperature. This mixture is then stirred at room temperature for 16 hours. The reaction mixture is poured into water and the α-sulfo-(4-hydroxybenzene)acetic acid is recovered from the aqueous solution by evaporation of the dioxane and ethylene chloride.

α-Sulfo-4-hydroxybenzeneacetic acid, 0.3 mole, is dissolved in aqueous sulfuric acid (50%). One equivalent of dichloromethyl ether is added to the solution maintained at between 35° to 45° C. Hydrogen chloride is then bubbled through this reaction mixture for 3 hours. The desired compound is recovered by pouring the reaction mixture into water and extracting the title compound with ethyl acetate. The ethyl acetate is dried over magnesium sulfate. The magnesium sulfate is removed by filtration and evaporation of the ethyl acetate gives the desired compound.

EXAMPLE 7

α-(Aminocarbonyl)amino-3-(chloromethyl)-4-hydroxybenzeneacetic acid

To about 0.15 mole of α-amino-4-hydroxybenzeneacetic acid dissolved in 700 ml of water and 0.2 mole of glacial acetic acid is added about 0.2 mole of potassium cyanate. The resulting mixture is stirred at room temperature for about 30 minutes. The reaction mixture is saturated with sodium chloride and then extracted with ethyl acetate. The ethyl acetate is washed with water, dried over magnesium sulfate, filtered and evaporated to give α-(aminocarbonyl)amino-4-hydroxybenzeneacetic acid Equivalent amounts (0.1 mole) of α-(aminocarbonyl)amino-4-hydroxybenzeneacetic acid and formaldehyde as a 34–38% formalin solution are added to 250 ml of concentrated hydrochloric acid. The temperature is maintained between 20° to 40° C. and gaseous hydrogen chloride is added over a period of 2 hours. The solution thus obtained is concentrated under vacuum and the residue is extracted with ethyl acetate. The ethyl acetate extract is washed with water, dried over magnesium sulfate and evaporated to give the title compound.

EXAMPLE 8

(−)-α-Amino-3-(azidomethyl)-4-hydroxybenzeneacetic acid

To a solution of (−)-α-amino-3-(chloromethyl)-4-hydroxybenzeneacetic acid (252 mg, 1 mmole) in 4 ml of methyl alcohol is added sodium azide (156 mg, 2.4 mmole). The mixture is stirred at about 40° C. for 15 minutes. After about 10 minutes the title compound begins to precipitate. The mixture is cooled, filtered and the product is washed with a small amount of methyl alcohol and acetone. The title compound is collected (210 mg, 95% yield). M.P. >300°; $[\alpha]_D^{18} = -73.03°$ (c 1.7, water), NMR (DMSO-$D_6$) ppm (δ) 4.22 (s,1), 4.35 (s,2), 6.7-7.5 (superimposed q and s,3).

Anal. calcd for $C_9H_{10}N_4O_3$: N 25.21; Found N, 23.83

EXAMPLE 9

(−)-α-Amino-3-(thiocyanatomethyl)-4-hydroxybenzeneacetic acid

A solution of (−)-α-amino-3-(chloromethyl)-4-hydroxybenzeneacetic acid (0.5 g, 1.98 mmole) and potassium thiocyanate (0.4 g, 4.12 mmole) in 10 ml of methanol is stirred at room temperature for 16 hours. The reaction mixture is filtered to remove the potassium chloride, the filtrate is evaporated and to the residue is added saturated aqueous sodium bicarbonate until the pH is 7. The title compound precipitates as a white powder which is filtered and dried. (1.83 g, 78% yield), NMR (TFA-D+$D_2O$) ppm (δ) 4.1 (s,2), 5.08 (s,1), 6.9-7.3 (m,3).

EXAMPLE 10

(−)-α-Amino-4-hydroxy-3-(methoxymethyl)benzeneacetic acid methyl ester hydrochloride A solution of (−)-α-amino-3-(chloromethyl)-4-hydroxybenzeneacetic acid (1 g, 3.96 mmole) in 10 ml of methanol is refluxed for 30 hours. The solvent is then removed under vacuum and the title compound is isolated in quantitative yield as a hygroscopic powder.

NMR (DMSO-$D_6$+$D_2O$) ppm (δ) 3.40 (s,3), 3.78 (s,3), 4.47 (s,2), 5.20 (s,1), 7.0-7.7 (m,3).

EXAMPLE 11

(−)-α-Amino-4-hydroxy-3-(methoxymethyl)benzeneacetic acid methyl ester (−)-α-Amino-4-hydroxy-3-(methoxymethyl)benzeneacetic acid methyl ester hydrochloride is dissolved in a minimum amount of methanol. To this solution is added methanolic potassium hydroxide until a basic reaction to phenolphthalein is observed. The potassium chloride which precipitates is removed and the solvent is removed under vacuum to give a quantitative yield of the title compound.

NMR (DMSO-$D_6$+$D_2O$) ppm (δ) 3.32 (s,3), 3.64 (s,3), 4.4 (superimposed s,2 and s,1), 6.6-7.3 (m,3).

EXAMPLE 12

(−)-α-Amino-4-hydroxy-3-(methoxymethyl)benzeneacetic acid (−)-α-Amino-4-hydroxy-3-(methoxymethyl)benzeneacetic acid methyl ester is dissolved in aqueous 1 N sodium hydroxide and the solution is stirred at 40°-50° C. for 1 hour. The solution is acidified with 6 N hydrochloric acid to a pH of 7. Evaporation of the solvent gives the title compound in a 90% overall yield.

NMR ($D_2O$) ppm (δ) 3.42 (s,3), 4.56 (s,2), 5.2 (s,1), 7.0-7.5 (m,3).

EXAMPLE 13

(−)-α-Amino-3-[[(aminoiminomethyl)thio]methyl]-4-hydroxybenzeneacetic acid dihydrochloride A solution of (−)-α-amino-3-(chloromethyl)-4-hydroxybenzeneacetic acid (2 g, 8 mmole) and thiourea (0.61 g, 8 mmole) in 10 ml of water is stirred at room temperature for 4 hours. Removal of the solvent by lyophilyzation gives a quantitative yield of the title compound, isolated as its dihydrochloride, $[\alpha]_D^{25} = -69.2°$ (c, 10.4, $H_2O$), NMR (TFA-D) 4.34 (s,2), 5.4 (s,1), 6.8-7.6 (m,3).

EXAMPLE 14

(−)-α-Amino-3-[[(4,5-dihydro-1H-imidazol-2-yl)thio]methyl]hydroxybenzeneacetic acid dihydrochloride The title compound as its dihydrochloride is obtained as described in Example 13 when thiourea is replaced by 2-imidazolidinethione. $[\alpha]_D^{25} = -53.41°$ (c, 9.4, $H_2O$), NMR (TFA-D+$D_2O$) ppm (δ) 4.05 (s,4), 4.41 (s,2), 5.16 (s,1), 6.9-7.7 (m,3).

EXAMPLE 15

(−)-α-Amino-4-hydroxy-3-[[(2-methyl-1H-tetrazol-5-yl)thio]methyl]benzeneacetic acid hydrochloride The title compound as its hydrochloride is obtained by the procedure described in Example 13 when thiourea is replaced by 1-methyl-1H-tetrazol-5-ylthiol.

$[\alpha]_D^{25} = -47.8°$ (c 11.86, $H_2O$), NMR (TFA−D+$D_2O$) 3.96 (s,3), 4.42 (s,2), 5.17 (s,1), 6.8−7.6 (m,3).

EXAMPLE 16

(−)-α-Amino-4-hydroxy-3-(sulfomethyl)benzeneacetic acid monosodium salt

The title compound is obtained after an aqueous solution of sodium sulfite (4 mmole) and (−)-α-amino-3-(chloromethyl)-4-hydroxybenzene (1 g, 4 mmole) in 15 ml of water is refluxed for 3 hours. Lyophilyzation of the solvent gives the title compound as its sodium salt.

NMR (TFA−D+$D_2O$) ppm (δ) 4.1 (s,2), 5.0 (s,1), 6.7−7.4 (m,3).

EXAMPLE 17

(−)-α-Amino-3-[[[[(aminoiminomethyl)amino]iminomethyl]thio]methyl]-4-hydroxybenzeneacetic acid dihydrochloride A solution of (−)-α-amino-3-(chloromethyl)-4-hydroxybenzeneacetic acid (1 g, 0.4 mmole) and N-(aminoiminomethyl)thiourea (0.47 g, 4 mmole), in 10 ml of water is stirred at room temperature for 4.5 hours. Removal of the solvent by lyophilyzation gives a quantitative yield of the title compound, isolated as its dihydrochloride.

NMR (TFA−D+$D_2O$) ppm (δ) 4.2 (s,2), 5.2 (s,1), 6.8−7.3 (m,3).

EXAMPLE 18

(−)-α-Amino-4-hydroxy-3-(hydroxymethyl)benzeneacetic acid

To a solution of (−)-α-amino-3-(chloromethyl)-4-hydroxybenzeneacetic acid hydrochloride in water is added saturated aqueous sodium bicarbonate until a pH of 7 is reached. The solution is stirred overnight and is then lyophilized to give a quantitative yield of the title compound, combined with 2 equivalents of sodium chloride.

NMR (TFA−D+$D_2O$) ppm (δ) 4.73 (s,2), 5.1 (s,1), 6.9−7.3 (m,3).

EXAMPLE 19

(−)-α-Amino-4-hydroxy-3-[(methylthio)methyl]benzeneacetic acid

To a solution of methanethiol (3 g, 0.04 mmole) in 250 ml of water is added sodium hydroxide (0.04 mole) followed by (−)-α-amino-3-(chloromethyl)-4-hydroxybenzeneacetic acid hydrochloride (5 g, 0.02 mole). The solution obtained is stirred overnight. Removal of the solvent by flash evaporation gives a quantitative yield of the title compound combined with 2 equivalents of sodium chloride.

NMR (TFA−D+$D_2O$) ppm (δ) 2.14 (s,3), 3.78 (s,2), 5.18 (s,1), 6.9−7.3 (m,3).

EXAMPLE 20

(−)-α-Amino-3-[[(ethoxythioxomethtyl)thio]methyl]-4-hydroxybenzeneacetic acid

To a solution of (−)-α-amino-3-(chloromethyl)-4-hydroxybenzeneacetic acid hydrochloride (1 g, 0.004 mole) in 20 ml of water is added carbonodithioic acid, O-ethyl ester, potassium salt (1.26 g, 0.08 mole). Within a few minutes a precipitate begins to form. The mixture is stirred at room temperature for 3 hours. The solid precipitate is filtered, washed with water and dried to give 58.3% of the title compound.

$[\alpha]_D^{25} = -81.1°$ ($CH_3OH$, c 5.82), NMR (TFA−D+$D_2O$) ppm (δ) 1.4 (t,3), 4.37 (s,2), 4.6 (q,2), 5.03 (s,2), 6.7−7.5 (m,3).

EXAMPLE 21

3-Azidomethyl-4-hydroxybenzeneacetic acid

A solution of 3-chloromethyl-4-hydroxybenzeneacetic acid (0.1 mole) and sodium azide (0.1 mole) in 250 ml of water is stirred at room temperature for about 16 hours. Removal of the solvent gives the title compound combined with sodium chloride.

Using the procedure described above, the following products are obtained from the thus listed starting materials.

| STARTING MATERIALS SUBSTITUTED BENZENEACETIC ACIDS | NUCLEOPHILE | PRODUCT |
| --- | --- | --- |
| α-Hydroxy-3-(chloromethyl)-4-hydroxybenzeneacetic acid | Thiourea | α-Hydroxy-3-[[(aminoiminomethyl)thio]methyl]-4-hydroxybenzeneacetic acid |
| α-Carboxy-3-bromomethyl-4-hydroxybenzeneacetic acid | Potassium methylthiolate | α-Carboxy-4-hydroxy-3-[(methylthio)methyl]benzeneacetic acid |
| α-Sulfo-3-chloromethyl-4-hydroxybenzeneacetic acid | Ammonium cyanate | α-Sulfo-3-(cyanatomethyl)-4-hydroxybenzeneacetic acid |
| α-(Aminocarbonyl)amino-3-chloromethyl-4-hydroxybenzeneacetic acid | Sodium cyanide | α-(Aminocarbonyl)amino-3-(cyanomethyl)-4-hydroxybenzeneacetic acid |
| α-Amino-3-(chloromethyl)-4-hydroxybenzeneacetic acid | Calcium cyanamide | α-Amino-3-(cyanoamino)methyl]-4-hydroxybenzeneacetic acid |
| α-Amino-3-(chloromethyl)-4-hydroxybenzeneacetic acid | Thiosemicarbazide | α-Amino-3-[[(aminohydrazonomethyl)thio]methyl]-4-hydroxybenzeneacetic acid |
| α-Amino-3-(chloromethyl)-4-hydroxybenzeneacetic acid | Formylthiosemicarbazide | α-Amino-3-[[[amino(formylhydrazono)methyl]thio]methyl]-4-hydroxybenzeneacetic acid |
| α-Amino-3-(chloromethyl)-4-hydroxybenzeneacetic acid | 2-Pyridinethiol | α-Amino-4-hydroxy-3-[(2-pyridinylthio)methyl]benzeneacetic acid |
| α-Amino-3-(chloromethyl)-4-hydroxybenzeneacetic acid | 1,3,4-thiadiazol-2-ylthiol | α-Amino-4-hydroxy-3-[(1,3,4-thiadiazol-2-ylthio)methyl]- |

-continued

| STARTING MATERIALS SUBSTITUTED BENZENEACETIC ACIDS | NUCLEOPHILE | PRODUCT |
| --- | --- | --- |
| α-Amino-3-(chloromethyl)-4-hydroxybenzeneacetic acid | 1,2,4-triazol-3-ylthiol | benzeneacetic acid α-Amino-4-hydroxy-3-[(1,2,4-triazol-3-ylthio)methyl]benzeneacetic acid |
| α-Amino-3-(chloromethyl)-4-hydroxybenzeneacetic acid | $Na_2S$ | α-Amino-4-hydroxy-3-(mercaptomethyl)benzeneacetic acid |
| α-Amino-3-(chloromethyl)-4-hydroxybenzeneacetic acid | $NH_2CS_2NH_4$ | α-Amino-3-[[(aminothioxomethyl)thio]methyl]-4-hydroxybenzeneacetic acid |

EXAMPLE 22

α-(Aminocarbonyl)amino-4-hydroxy-3-methylbenzeneacetic acid

A mixture of α-(aminocarbonyl)amino-3-chloromethyl-4-hydroxybenzeneacetic acid (0.1 mole) and 10% Pd on charcoal (1 g) catalyst in 50 ml of water is subjected to hydrogen gas at a pressure of about 60 pounds/in$^2$ at room temperature for a period of about 16 hours. Removal of the catalyst followed by evaporation of the water gives the title compound.

EXAMPLE 23

The following three procedures may be used to prepare compounds of Formula 1 wherein $R_2$ is tert-butyloxycarbonyl from the corresponding compounds wherein $R_2$ is hydrogen.

PROCEDURE I

To a mixture of an amino acid (40 mmole) and magnesium oxide (80 mmole) in 100 ml of 50% dioxane-water is added t-butyloxycarbonylazide (80 mmole). The mixture is stirred for 16–20 hours at 45°–50° C., it is then cooled, diluted with 400 ml of water and is extracted three times with ethyl acetate. The organic phase is subsequently washed with two portions of 20 ml of 1 N sodium bicarbonate and twice with water. The combined aqueous layers are cooled to 5° C. and acidified to pH 5 with cold 10% aqueous citric acid. The solution obtained is saturated with sodium chloride and is extracted with three portions of 400 ml of ethyl acetate. The organic phase is then dried over sodium sulfate, and the solent is removed under vacuum. The desired N-tert-butyloxycarbonyl amino acid is thus isolated as an oil or a solid foam.

PROCEDURE II

To a solution of an amino acid (10 mmole) and triethylamine (15 mmole) in 12 ml of 50% water-dioxane is added 2-(tert-butyloxycarbonyloxyimino)-2-phenylacetonitrile (BOC-ON) (11 mmole). The mixture is stirred at room temperature for three hours. To the homogeneous mixture thus obtained, water (15 ml) and ethyl acetate (20 ml) are added. The aqueous phase is separated, washed with ethyl acetate (20 ml), acidified with 5% aqueous citric acid solution and extracted with ethyl acetate. The organic phase is dried and the solvent is removed under vacuum to give the N-tert-butyloxycarbonyl amino acid as an oil or a solid foam.

PROCEDURE III

To a well stirred solution of an amino acid (0.5 mole) and sodium hydroxide (0.5 mole) in 50 ml of water and 100 ml of tert-butanol is added di-tert-butyl dicarbonate [$(BOC)_2O$](0.55 mole). The mixture is stirred overnight. The turbid solution obtained is diluted with water (250 ml) and is extracted with three portions of pentane (300 ml each). The aqueous phase is cooled, acidified to pH 2–3 with potassium hydrogen sulfate, and is extracted with four 400 ml portions of ethyl acetate. The combined organic phase is dried over anhydrous sodium sulfate, filtered and the solvent removed under reduced pressure. The desired N-tert-butyloxycarbonyl amino acid is thus obtained as an oil or a solid foam.

EXAMPLE 24

(−)-3-(Azidomethyl)-(tert-butyloxycarbonylamino)-4-hydroxybenzeneacetic acid

The title compound is obtained in 55% yield by Procedure I, Example 23, from (−)-α-amino-3-azidomethyl-4-hydroxybenzeneacetic acid.

NMR (CDCl$_3$) ppm (δ) 1.21 (s,9), 1.44 (s,2), 5.05 (broad s,1), 6.5–7.2 (m,3).

EXAMPLE 25

(−)-α(tert-Butyloxycarbonylamino)-4-hydroxy-3-(methoxymethyl)benzeneacetic acid

The title compound is obtained in 72% yield by Procedure I or in 83% yield by Procedure II, Example 23, from (−)-α-amino-4-hydroxy-3-(methoxymethyl)benzeneacetic acid.

NMR (CDCl$_3$) ppm (δ) 1.35 (s,9), 3.40 (s,3), 4.60 (s,2), 5.2 (broad s,1), 6.6–7.5 (m,3).

EXAMPLE 26

α-(tert-Butyloxycarbonylamino)[4-hydroxy-3-[(1-methyl-1H-tetrazol-5-yl)thio]methyl]benzeneacetic acid The title compound is obtained in 30% yield by Procedure III, Example 23, from (−)-α-amino-4-hydroxy-3-[[(1-methyl-1H-tetrazol-5-yl)thio]methyl]benzeneacetic acid.

NMR (CDCl$_3$) ppm (δ) 1.37 (s,9), 3.7 (s,2), 3.8 (s,3), 5.15 (broad s,1), 6.8–7.4 (m,3).

EXAMPLE 27

(−)-(tert-Butyloxycarbonylamino)-3-(hydroxymethyl)-4-hydroxybenzeneacetic acid

The title compound is obtained in 76% yield by Procedure II, Example 23, from (−)-α-amino-4-hydroxy-3-(hydroxymethyl)benzeneacetic acid.

NMR (DMSO−D$_6$+D$_2$O) ppm (δ) 1.4 (s,9), 4.62 (s,2), 5.1 (s,1), 6.8–7.6 (m,3).

EXAMPLE 28

(—)-(tert-Butyloxycarbonylamino)-4-hydroxy-3-[(methylthio)methyl]benzeneacetic acid The title compound is obtained in 81% yield by Procedure III, Example 23, from (—)-α-amino-4-hydroxy-3-[(methylthio)methyl]benzeneacetic acid.

NMR (CDCl$_3$) ppm (δ) 1.4 (s,9), 1.97 (s,3), 3.68 (s,2), 5.1 (broad s,1), 6.6–7.5 (m,3).

EXAMPLE 29

(—)-α-tert-Butyloxycarbonylamino-3-[[(ethoxythioxomethyl)thio]methyl]-4-hydroxybenzeneacetic acid The title compound is obtained in 91.5% yield when prepared according to Procedure III, Example 23, from (—)-α-amino-3-[[(ethoxythioxomethyl)thio]methyl]-4-hydroxybenzeneacetic acid.

NMR (CDCl$_3$) ppm (δ) 1.3–1.5 (superimposed t,3 and s,9), 4.21 (s,2), 4.5 (q,2), 4.96 (broad s,1), 6.4–7.2 (m,3).

EXAMPLE 30

(—)-α-Amino-4-hydroxy-3-[(methylsulfinyl)methyl]-benzeneacetic acid

To an aqueous solution (500 ml) of α-amino-4-hydroxy-3-[(methylthio)methyl]benzeneacetic acid (1 mole) is added sodium metaperiodate (1 mole). The mixture is stirred at room temperature for 5 hours, it is filtered and the filtrate is lyophilyzed to give a quantitative yield of the title compound.

NMR (DMSO—D$_6$+D$_2$O) ppm (δ) 2.65 (s,3), 4.12 (s,2), 4.5 (s,1), 6.8–7.5 (m,3).

EXAMPLE 31

(—)-α-Amino-4-hydroxy-3-[(methylsulfonyl)methyl]-benzeneacetic acid

A solution of α-amino-4-hydroxy-3-[(methylthio)methyl]benzeneacetic acid (3 g, 8.7 mmole) and 30 ml of 30% hydrogen peroxide in 300 ml of acetic acid is stirred at room temperature for 17 hours. The mixture is filtered and the filtrate is flash concentrated at 35° C. It is mixed with methanol to give a solid which is washed with ether, filtered and dried to give the title compound in 92% yield [α]$_D^{25}$ = —82.07° (dilute HCl, C 9.48).

NMR (TFA—D+D$_2$O) 2.75 (s,3), 4.17 (s,2), 4.8 (s,1), 6.5–7.3 (m,3).

EXAMPLE 32

(—)-α-tert-Butoxycarbonylamino-4-hydroxy-3-[(methylsulfinyl)methyl]benzeneacetic acid The title compound is obtained in 31% yield when prepared from (—)-α-amino-4-hydroxy-3-[(methylsulfinyl)methyl]benzeneacetic acid according to Procedure III in Example 23.

NMR (DMSO—D$_6$) ppm (δ) 1.4 (s,9), 5.47 (s,3), 4.0 (s,2), 4.98 (m,1), 6.5–7.5 (m,3).

EXAMPLE 33

(—)-α-tert-Butyloxycarbonylamino-4-hydroxy-3-[(methylsulfonyl)methyl]benzeneacetic acid The title compound is obtained in 36% yield when prepared according to Procedure III as described in Example 23 from (—)-α-amino-4-hydroxy-3-[(methylsulfonyl)methyl]benzeneacetic acid.

NMR (CDCl$_3$) ppm (δ) 1.36 (s,9), 2.67 (s,3), 4.3 (s,2), 5.15 (broad s,1), 6.5–7.4 (m,3).

EXAMPLE 34

General procedures for the coupling of carboxylic acids with 7-aminocephalosporins

PROCEDURE IV

Equimolar quantities of a compound of Formula 3 wherein W is H or a protected —NH$_2$, —CO$_2$H, —SO$_3$H or —OH group and X is other than —SO$_3$H, a compound of Formula 2 wherein R$_{11}$ is a tert-butyl group (prepared according to the general procedure described in J. Med. Chem., 9, 444 (1966)), and N-ethoxycarbonyl-2-ethoxy-1,2-dihydroquinoline [EEDQ] in dry chloroform is stirred at room temperature for from 6 to 24 hours. The solvent is evaporated and the residue is chromatographed on silica gel and eluted with 1:1 ether:chloroform. A compound of Formula 1 wherein R$_{11}$ is a tert-butyl group is obtained upon evaporation of the solvent.

PROCEDURE V

A compound of Formula 3 wherein W is hydrogen, —CO$_2$H, —SO$_3$H and —OH or —NH$_2$ which are protected and X is other than —SO$_3$H, Cl or Br, is converted to a mixed anhydride upon treatment with an equimolar amount of isobutyl chloroformate or pivaloyl chloride in the presence of an equimolar amount of tertiary amine such as triethyl amine, in a suitable solvent such as tetrahydrofuran, chloroform, at a temperature of from —10° C. to 20° C. for a period of from 0.5 to 1 hour.

To the thus obtained mixture is added a solution of an equimolar amount of a compound of Formula 2 in a suitable solvent such as water or water-tetrahydrofuran, containing 1 equivalent of an acid acceptor such as triethylamine or sodium bicarbonate at a temperature of from 0° to about 40° C. for from 0.5 to about 6 hours. The organic solvent is removed and the pH is adjusted to about 3 with hydrochloric acid. The coupled compound is extracted with ethyl acetate. The ethyl acetate is dried, filtered and evaporated to give a coupled cephalosporin derivative in the form of a solid. This procedure is adapted from the general procedure described in J. Med. Chem., 9, 746 (1966).

PROCEDURE VI

A compound of Formula 3 wherein W is hydrogen, —CO$_2$H or —SO$_3$H or a protected —NH$_2$ or —OH group may be converted to the acid chloride by reacting the acid with 1.05 equivalents of thionyl chloride in ethyl ether in the presence of a catalytic amount of dimethylformamide. The reaction mixture is refluxed for about 3 hours and then the solvent and any excess thionyl chloride.

The thus formed acid chloride (0.05 mole) corresponding to a compound of Formula 3 is added to 100 ml of dry tetrahydrofuran. To this solution is added 1 equivalent of a 7-aminocephalosporin derivative dissolved in 100 ml of 1:1 tetrahydrofuran:water which contains 1 equivalent of an acid acceptor such as triethylamine or sodium bicarbonate. The resulting mixture is stirred at room temperature for from 30 minutes to 3 hours. About 100 ml of water is added and the tetrahydrofuran is removed under vacuum. The pH is adjusted to about 3 to 5 with hydrochloric acid. Ethyl acetate is used to extract the compound of Formula 1 from the aqueous solution. The ethyl acetate is dried over magnesium sulfate, the sulfate is removed by filtration and the ethyl acetate is removed to give the cephalosporin compound.

EXAMPLE 35

7-[[(tert-Butyloxycarbonylamino)-[4-hydroxy-3-(methoxymethyl)phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid The title compound is obtained in 38% yield by Procedure V when the reagents used are (−)-α-(tert-butyloxycarbonylamino)-3-(methoxymethyl)-4-hydroxybenzeneacetic acid and 7-amino-3-[[(1-methyl-1H-tetrazol-5-yl)thio]methyl]-8-oxo-5-thia-1-azabicyclo[4.2.0]oct-2-ene-2-carboxylic acid.

NMR (DMSO−$D_6$) 1.42 (s,9), 3.3 (s,3), 3.6 (m,2), 3.9 (s,3), 4.2 and 4.3 (superimposed broad s,2 and s,2), 5.03 (superimposed two d,2), 5.6 (q,1), 6.5−7.3 (m,3).

Anal. Calcd. for $C_{25}H_{31}N_7O_8S_2$: S, 10.32 Found: S, 11.03

EXAMPLE 36

7-[[(tert-Butyloxycarbonylamino)-[4-hydroxy-3-(methoxymethyl)phenyl]acetyl]amino]-3-methyl-8-oxo-5-thia-1-azabicyclo[4.2.0]oct-2-ene-2-carboxylic acid tert-butyl ester The title compound is obtained in 85.7% yield when prepared by Procedure IV from (−)-α-(tert-butyloxycarbonyl)-4-hydroxy-3-(methoxymethyl)benzeneacetic acid and 7-amino-3-methyl-8-oxo-5-thia-1-azabicyclo[4.2.0]oct-2-ene-2-carboxylic acid, tert-butyl ester.

NMR (CDCl$_3$) ppm (δ), 1.41 (s,9), 1.53 (s,9), 2.08 (s,3), 3.25 and 3.40 (superimposed q,2 and s,3), 4.52 (s,2), 4.81 (d,1), 5.1 (d,1), 5.6 (m,1), 6.2−7.2 (m,3).

EXAMPLE 37

7-[[(tert-Butyloxycarbonylamino)-[4-hydroxy-3-(methoxymethyl)phenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid The title compound is obtained in 55% yield by Procedure V when the reagents used are (−)-α-(tert-butyloxycarbonylamino)-4-hydroxy-3-(methoxymethyl)benzeneacetic acid and 7-amino-3-[[(5-methyl-1,3,4-thiadiazol-2-yl)thio]methyl]-8-oxo-5-thia-1-azabicyclo[4.2.0]oct-2-ene-2-carboxylic acid.

NMR (DMSO−$D_6$) ppm (δ) 1.4 (s,9), 2.63 (s,3), 3.25 (s,3), 3.46 (m,2), 4.33 (superimposed s,2 and m,2), 5.0 (m,2), 5.6 (m,1), 6.5−7.4 (m,3).

EXAMPLE 38

7-[[tert-Butyloxycarbonylamino)-[4-hydroxy-3-(methoxymethyl)phenyl]acetyl]amino]-8-oxo-3-[[(1H-1,2,3-triazol-5-yl)thio]methyl]-5-thia-1-azabicyclo[4.2.0]oct-2-ene-2-carboxylic acid The title compound is obtained in 40% yield by Procedure V when the reagents used are (−)-α-(tert-butyloxycarbonylamino)-4-hydroxy-3-(methoxymethyl)benzeneacetic acid and 7-amino-3-[[(1H-1,2,3-triazol-5-yl)thio]methyl]-8-oxo-5-thia-1-azabicyclo[4.2.0]oct-2-ene-2-carboxylic acid.

NMR (DMSO−$D_6$) ppm (δ) 1.4 (s,9), 3.25 (s,3), 3.46 (m,2), 3.8 (broad s,2), 4.3 (s,2), 5.0 (superimposed two d,2), 5.6 (m,1), 6.5−7.3 (m,3), 7.9 (s,1).

EXAMPLE 39

7-[[(3-Azidomethyl-4-hydroxyphenyl)-(tert-butyloxycarbonylamino)acetyl]amino]-3-[[(1-methyl-1H-tetrazol-5-yl)thio]methyl]-8-oxo-5-thia-1-azabicyclo[4.2.0]oct-2-ene-2-carboxylic acid The title compound is obtained in 25% yield by Procedure V when the reagents used are (−)-3-(azidomethyl)-α-(tert-butyloxycarbonylamino)-4-hydroxybenzeneacetic acid and 7-amino-3-[[(1-methyl-1H-tetrazol-5-yl)thio]methyl]-8-oxo-5-thia-1-azabicyclo[4.2.0]oct-2-ene-2-carboxylic acid.

NMR (DMSO−$D_6$) ppm (δ) 1.38 (s,9), 3.55 (m,2), 3.87 (s,3), 4.28 (m,2), 4.98 (m,2), 5.6 (m,1), 6.7−7.4 (m,3).

EXAMPLE 40

7-[[(3-Azidomethyl-4-hydroxyphenyl)-(tert-butyloxycarbonylamino)acetyl]amino]-3-methyl-8-oxo-5-thia-1-azabicyclo[4.2.0]oct-2-ene-2-carboxylic acid tert-butyl ester The title compound is obtained in 70% yield when prepared by Procedure IV from (−)-3-(azidomethyl)-α-(tert-butyloxycarbonylamino)-4-hydroxybenzeneacetic acid and 7-amino-3-methyl-8-oxo-5-thia-1-azabicyclo[4.2.0]oct-2-ene-2-carboxylic acid, tert-butyl ester.

NMR (CDCl$_3$) ppm (δ) 1.40 (s,9), 1.50 (s,9), 2.0 (s,3), 3.14 (q,2), 4.35 (s,2), 4.80 (d,1), 5.22 (broad d,1), 5.8 (m,1), 6.6−73. (m,3).

EXAMPLE 41

7-[[(3-Azidomethyl-4-hydroxyphenyl)-(tert-butyloxycarbonylamino)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid The title compound is obtained in 42% yield by Procedure V when the reagents used are (−)-3-(azidomethyl)-α-(tert-butyloxycarbonylamino)-4-hydroxybenzeneacetic acid and 7-amino-3-[[(5-methyl-1,3,4-thiadiazol-2-yl)thio]methyl]-8-oxo-5-thia-1-azabicyclo[4.2.0]oct-2-ene-2-carboxylic acid.

NMR (DMSO−$D_6$) ppm (δ) 1.4 (s,9), 2.66 (s,3), 3.55 (m,2), 4.28 (m,2), 4.98 (m,2), 5.6 (m,1), 6.7−7.4 (m,3).

EXAMPLE 42

7-[[(tert-Butyloxycarbonylamino)-[4-hydroxy-3-[(methylthio)methyl]phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid The title compound is obtained in 57.8% yield by Procedure V when the reagents used are (−)-α-(tert-butyloxycarbonylamino)-3-[(methylthio)methyl]-4-hydroxybenzeneacetic acid and 7-amino-3-[[(1-methyl-1H-tetrazol-5-yl)thio]methyl]-8-oxo-5-thia-1-azabicyclo[4.2.0]oct-2ene-2-carboxylic acid.

NMR (DMSO−$D_6$) ppm (δ) 1.42 (s,9), 2.0 (s,3), 3.6 (m,2), 3.9 (s,3), 4.2 (broad s,2), 5.03 (superimposed two d,2), 5.6 (q,1), 6.5−7.3 (m,3).

EXAMPLE 43

7-[[(tert-Butyloxycarbonylamino)-[4-hydroxy-3-[(methylthio)methyl]phenyl]acetyl]amino]-3-methyl-8-oxo-5-thia-1-azabicyclo[4.2.0]oct-2-ene-2-carboxylic acid The title compound is obtained in 53.8% yield when prepared by Procedure V from (−)-α-(tert-butyloxycarbonylamino)-3-[(methylthio)methyl]-4-hydroxybenzeneacetic acid and 7-amino-3-methyl-8-oxo-5-thia-1-azabicyclo[4.2.0]-oct-2-ene-2-carboxylic acid.

NMR (DMSO—D$_6$) ppm ($\delta$) 1.41 (s,9), 2.04 (s,6), 3.40 (m,2), 3.5 (s,2), 4.95 (d,1), 5.1 (d,1), 5.6 (m,1), 6.2–7.2 (m,3).

EXAMPLE 44

7-[[(tert-Butyloxycarbonylamino)-[4-hydroxy-3-[(methylthio)methyl]phenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid The title compound is obtained in 24.5% yield by Procedure V when the reagents used are (—)-α-(tert-butyloxycarbonylamino)-3-[(methylthio)methyl]-4-hydroxybenzeneacetic acid and 7-amino-3-[[(5-methyl-1,3,4-thiadiazol-2-yl)thio]methyl]-8-oxo-5-thia-1-azabicyclo[4.2.0]oct-2-ene-2-carboxylic acid.

NMR (DMSO—D$_6$) ppm ($\delta$) 1.42 (s,9), 2.0 (s,3), 2.63 (s,3), 3.5 (broad s,4), 4.2 (m,2), 5.0 (m,2), 5.6 (m,1), 6.5–7.4 (m,3).

EXAMPLE 45

7-[[(tert-Butyloxycarbonylamino)-[4-hydroxy-3-[(methylthio)methyl]phenyl]acetyl]amino]-3-[(1H-1,2,3-triazol-5-yl)thio]methyl]-8-oxo-5-thia-1-azabicyclo[4.2.0]oct-2-ene-2-carboxylic acid The title compound is obtained in 19% yield by Procedure V from (—)-α-(tert-butyloxycarbonylamino)-[4-hydroxy-3-[(methylthio)methyl]benzeneacetic acid and 7-amino-3-[[(1H-1,2,3-triazol-5-yl)thio]methyl]-8-oxo-5-thia-1-azabicyclo[4.2.0]oct-2-ene-2-carboxylic acid.

NMR (DMSO—D$_6$) ppm ($\delta$) 1.4 (s,9), 2.0 (s,3), 3.6 (m,2), 4.0 (broad s,2), 5.0 (superimposed two d,2), 5.6 (q,1), 6.5–7.3 (m,3), 7.77 (s,1).

EXAMPLE 46

7-[[[[(tert-Butyloxycarbonylamino)-[4-hydroxy-3-(1-methyl-1H-tetrazol-5-yl)thio]methyl]phenyl]acetyl]amino]-3-methyl-8-oxo-5-thia-1-azabicyclo[4.2.0]oct-2-ene-2-carboxylic acid tert-butyl ester The title compound is obtained in 30% yield when prepared by Procedure IV from α-(tert-butyloxycarbonylamino)-4-hydroxy-3-[[(1-methyl-1H-tetrazol-5-yl)thio]methyl]benzeneacetic acid and 7-amino-3-methyl-8-oxo-5-thia-1-azabicyclo[4.2.0]oct-2-ene-2-carboxylic acid, tert-butyl ester.

NMR (CDCl$_3$) 1.43 (s,9), 1.50 (s,9), 2.0 (s,3), 3.17 (q,2), 3.75 (s,3), 4.37 (broad s,2), 4.76 (d,1), 5.08 (d,1), 5.7 (m,1), 6.5–7.4 (m,3).

EXAMPLE 47

7[[(tert-Butyloxycarbonylamino)-[[4-hydroxy-3-(methylsulfinyl)methyl]phenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid The title compound is obtained in 20.6% yield by Procedure V when the reagents used are α-tert-butyloxycarbonylamino-3-hydroxy-4-[(methylsulfinyl)methyl]benzeneacetic acid and 7-amino-3-[[(5-methyl-1,3,4-thiadiazol-2-yl)thio]methyl]-8-oxo-5-thia-1-azabicyclo[4.2.0]oct-2-ene-2-carboxylic acid.

NMR (DMSO—D$_6$) ppm ($\delta$) 1.4 (s,9), 2.4 (s,3), 2.63 (s,3), 3.55 (broad s,2), 3.9 (s,2), 4.2 (m,2), 4.93 (d,1), 5.1 (m,1), 5.5 (m,1), 6.5–7.5 (m,3).

EXAMPLE 48

7-[[(tert-Butyloxycarbonylamino)-[[4-hydroxy-3-(methylsulfonyl)methyl]phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid The title compound is obtained in 42.7% yield by Procedure V when the reagents used are α-tert-butyloxycarbonylamino-3-hydroxy-4-[(methylsulfonyl)methyl]benzeneacetic acid and 7-amino-3-[[(1-methyl-1H-tetrazol-5-yl)thio]methyl]-8-oxo-5-thia-1-azabicyclo[4.2.0]oct-2-ene-2-carboxylic acid.

NMR (DMSO—D$_6$) ppm ($\delta$) 1.42 (s,9), 2.84 (s,3), 3.6 (m,2), 3.9 (s,3), 4.2 (broad s,2), 5.0 (superimposed two d,2), 5.6 (m,1), 6.5–7.5 (m,3).

EXAMPLE 49

PROCEDURE VII

Removal of tert-butyloxycarbonyl and tert-butyl protecting groups from compounds of Formula 1

The appropriately substituted compound of Formula 1 which contains a tert-butyl ester group and a tert-butyloxycarbonyl group (0.5 g) is added to 10 ml of trifluoroacetic acid (TFA) (10 ml) at 0° to 10° C. After stirring the TFA mixture for 2 minutes, the excess TFA is removed under vacuum. The residue is triturated with a large excess of ethyl ether to give the tert-butyloxycarbonyl derivative of a compound of Formula 1 which contains a free acid group.

When, however, the above TFA solution is allowed to stir for 15 minutes at 0° to 10° C. and the TFA is removed under reduced pressue and the residue is triturated with ethyl ether, both the tert-butyl ester and the tert-butylcarbonyl groups are removed from the compound of Formula 1. The desired compound is isolated as the trifluoroacetate salt.

When a compound of Formula 1 (0.5 g), wherein R$_1$ and R$_{11}$ are both tert-butyl groups, is subjected to 10 ml of TFA for 2 minutes, both tert-butyl groups are removed and a compound of Formula 1 wherein R$_1$ and R$_{11}$ are both hydrogen is obtained.

Optionally, it is possible to prepare the free amino acid from the corresponding trifluoroacetic acid salt. The trifluoroacetic acid salt of a compound of Formula 1 wherein W is amino and R$_{11}$ is hydrogen (1 g) is dissolved in 150 ml of 1:1 methanol:water. To this is added amberlite IR45 resin until the pH is between 3 to 5. The mixture is filtered to remove the resin and the solvents are evaporated to give the free amino acid.

EXAMPLE 50

7-[[Amino[3-(Azidomethyl)-4-hydroxyphenyl]acetyl]amino]-3-methyl-8-oxo-5-thia-1-azabicyclo[4.2.0]oct-2-ene-2-carboxylic acid The title compound is obtained in quantitative yield upon dissolving the 7-[[[3-(azidomethyl)-4-hydroxyphenyl](tert-butyloxycarbonylamino)acetyl]amino]-3-methyl-8-oxo-5-thia-1-azabicyclo[4.2.0]oct-2-ene-2-carboxylic acid, tert-butyl ester in trifluoroacetic acid for 2 minutes as described in Procedure VII.

NMR (TFA-D) ppm ($\delta$) 1.35 (s,9), 2.0 (s,3), 3.1 (m,2), 4.20 (s,2), 4.85 (d,1), 5.13 (broad s,1), 5.4 (d,1), 6.6–7.3 (m,3).

EXAMPLE 51

7-[[Amino[4-hydroxy-3-(methoxymethyl)phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid trifluoroacetate The title compound is obtained in quantitative yield as described in Procedure VII from 7-[[(tert-butyloxycarbonylamino)-[4-hydroxy-3-(methoxymethyl)phenyl]acetyl]amino]-3-[[(1-methyl-1H-tetrazol-5-yl)thio]methyl]-8-oxo-5-thia-1-azabicyclo[4.2.0]oct-2-ene-2-carboxylic acid.

NMR (TFA-D) ppm ($\delta$) 3.6 (s,3), superimposed on 3.7 (m,2), 4.03 (s,3), 4.7 (m,2), superimposed on 4.75 (s,2), 5.1 (d,1), 5.42 (s,1), 5.76 (d,1), 6.8–7.5 (m,3).

EXAMPLE 52

7-[[Amino[4-hydroxy-3-(methoxymethyl)phenyl]acetyl]amino]-3-methyl-8-oxo-5-thia-1-azabicyclo[4.2.0]oct-2-ene-2-carboxylic acid trifluoroacetate The title compound is obtained in 91% yield as described in Procedure VII from 7-[[(tert-butyloxycarbonylamino)-[4-hydroxy-3-(methoxymethyl)phenyl]acetyl]amino]-3-methyl-8-oxo-5-thia-1-azabicyclo[4.2.0]oct-2-ene-2-carboxylic acid tert-butyl ester.

NMR (TFA-D) 2.2 (s,3), 3.4 (q,2), superimposed on 3.5 (s,3), 4.6 (s,2), 5.07 (d,1), 5.3 (s,1), 5.6 (d,1), 6.6–7.5 (m,3).

EXAMPLE 53

7-[[Amino[4-hydroxy-3-(methoxymethyl)phenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid trifluoroacetate The title compound is obtained in quantitative yield as described in Procedure VII from 7-[[(tert-butyloxycarbonylamino)-[4-hydroxy-3-(methoxymethyl)phenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid.

NMR (TFA−D+D$_2$O) ppm ($\delta$) 3.04 (s,3), 3.5 (superimposed s,3 and m,2), 4.5 (m,2), 4.63 (s,2), 5.08 (d,1), 5.35 (s,1), 5.75 (d,1), 6.7–7.5 (m,3).

EXAMPLE 54

7-[[Amino[4-hydroxy-3-(methoxymethyl)phenyl]acetyl]amino]-8-oxo-3-[(1H-1,2,3-triazol-5-ylthio)methyl]-5-thia-1-azabicyclo[4.2.0]oct-2-ene-2-carboxylic acid trifluoroacetate The title compound is obtained in quantitative yield as described in Procedure VII from 7-[[(tert-butyloxycarbonylamino)-[4-hydroxy-3-(methoxymethyl)phenyl]acetyl]amino]-8-oxo-3-[(1H-1,2,3-triazol-5-ylthio)methyl]-5-thia-1-azabicyclo[4.2.0]oct-2-ene-2-carboxylic acid.

NMR (TFA-D) ppm ($\delta$) 3.6 (s,3), superimposed on 3.7 (m,2), 4.7 (m,2) superimposed on 4.8 (s,2), 5.1 (d,1), 5.5 (s,1), 5.5 (d,1), 6.8–7.5 (m,3), 8.3 (s,1).

EXAMPLE 55

7-[[Amino[3-(azidomethyl)-4-hydroxyphenyl]acetic]amino]-3-[[(1-methyl-1H-tetrazol-5-yl)thio]methyl]-8-oxo-5-thia-1-azabicyclo[4.2.0]oct-2-ene-2-carboxylic acid trifluoroacetate The title compound is obtained in quantitative yield as described in Procedure VII from 7-[[[3-(azidomethyl)-4-hydroxyphenyl]-(tert-butyloxycarbonylamino)acetyl]amino]-3-[[(1-methyl-1H-tetrazol-5-yl)thio]methyl]-8-oxo-5-thia-1-azabicyclo[4.2.0]oct-2-ene-2-carboxylic acid.

NMR (TFA-D) ppm ($\delta$) 3.8 (m,2), 4.18 (s,3), 4.6 (s,2), superimposed on 4.7 (m,2), 5.3 (d,1), 5.55 (s,1), 5.84 (d,1), 6.8–7.6 (m,3).

EXAMPLE 56

7-[[Amino[3-(azidomethyl)-4-hydroxyphenyl]acetyl]amino]-3-methyl-8-oxo-5-thia-1-azabicyclo[4.2.0]oct-2-ene-2-carboxylic acid trifluoroacetate The title compound is obtained in quantitative yield as described in Procedure VII by dissolving 7-[[[3-(azidomethyl)-4-hydroxyphenyl]-(tert-butyloxycarbonylamino)acetyl]amino]-3-methyl-8-oxo-5-thia-1-azabicyclo[4.2.0]oct-2-ene-2-carboxylic acid tert-butyl ester and stirring for 15 minutes.

NMR (TFA-D) 2.18 (s,3), 3.25 (broad s,2), 4.36 (s,2), 5.0 (d,1), 5.23 (s,1), 5.43 (d,1), 6.6–7.6 (m,3).

EXAMPLE 57

7-[[Amino[3-(azidomethyl)-4-hydroxyphenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid trifluoroacetate The title compound is obtained in quantitative yield as described in Procedure VII from 7-[[(3-azidomethyl-4-hydroxyphenyl)-(tert-butyloxycarbonylamino)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid.

NMR (TFA−D+D$_2$O) 3.1 (s,3), 3.5 (m,2), 4.5 (m,2), 4.63 (s,2), 5.08 (d,1), 5.35 (s,1), 5.75 (d,1), 6.7–7.5 (m,3).

EXAMPLE 58

7-[[Amino-[4-hydroxy-3-[(methylthio)methyl]phenyl]acetyl]-amino]-3-[[(1-methyl-1H-tetrazol-5-yl)thio]methyl]-8-oxo-5-thia-1-azabicyclo[4.2.0]oct-2-ene-2-carboxylic acid trifuloroacetate The title compound is obtained in quantitative yield as described in Procedure VII from 7-[[(tert-butyloxycarbonylamino)-[4-hydroxy-3-[(methylthio)methyl]phenyl]-acetyl]amino]-3-[[(1-methyl-1H-tetrazol-5-yl)thio]methyl]-8-oxo-5-thia-1-azabicyclo[4.2.0]oct-2-ene-2-carboxylic acid.

NMR (TFA-D) ppm ($\delta$) 2.15 (s,3), 3.55 (m,2), 3.9 (s,3), 4.2 (m,2), 5.0 (m,2), 5.6 (m,1), 6.5–7.3 (m,3).

EXAMPLE 59

7-[[Amino[4-hydroxy-3-[(methylthio)methyl]phenyl]acetyl]-amino]-3-methyl-8-oxo-5-thia-1-azabicyclo[4.2.0]oct-2-ene-2-carboxylic acid trifluoroacetate The title compound is obtained in quantitative yield as described in Procedure VII from 7-[[(tert-butyloxycarbonylamino)-[4-hydroxy-3-[(methylthio)methyl]phenyl]-acetyl]amino]-3-methyl-8-oxo-5-thia-1-azabicyclo[4.2.0]oct-2-ene-2-carboxylic acid.

NMR (TFA−D+D$_2$O) ppm ($\delta$) 2.18 (s,3), 2.22 (s,3), 3.38 (m,2), 3.83 (s,2), 5.07 (d,1), 5.3 (s,1), 5.62 (d,1), 6.5–7.4 (m,3).

EXAMPLE 60

7-[[Amino[4-hydroxy-3-[(methylthio)methyl]phenyl]acetyl]-amino]-3-[[(5-methyl-1,3,4-thiadiazol-2-yl)thio]methyl]-8-oxo-5-thia-1-azabicyclo[4.2.0]oct-2-ene-2-carboxylic acid trifluoroacetate The title compound is obtained in quantitative yield as described in Procedure VII from 7-[[(tert-butyloxycarbonylamino)-[4-hydroxy-3-[(methylthio)methyl]phenyl]acetyl]-amino]-3-[[(5-methyl-1,3,4-thiadiazol-2-yl)thio]methyl]-8-oxo-5-thia-1-azabicyclo[4.2.0]oct-2-ene-2-carboxylic acid.

NMR (DMSO-$D_6$) ppm ($\delta$) 2.0 (s,3), 2.63 (s,3), 3.5 (broad s,4), 4.0 (m,2), 5.0 (m,2), 5.5 (m,1), 6.7–7.5 (m,3).

EXAMPLE 61

7-[[Amino-[4-hydroxy-3-[(methylthio)methyl]phenyl]acetyl]-amino]-3-[[(1$\underline{H}$-1,2,3-triazol-5-yl)thio]methyl]-8-oxo-5-thia-1-azabicyclo[4.2.0]oct-2-ene-2-carboxylic acid trifluoroacetate The title compound is prepared according to Procedure VII from 7-[[(tert-butyloxycarbonylamino[4-hydroxy-3-[(methylthio)methyl]phenyl]acetyl]amino]-3-[[(1$\underline{H}$-1,2,3-triazol-5-yl)thio]methyl]-8-oxo-5-thia-1-azabicyclo[4.2.0]oct-2-ene-2-carboxylic acid.

EXAMPLE 62

7-[[Amino[4-hydroxy-3-(1-methyl-1$\underline{H}$-tetrazol-5-yl)thio-methyl]phenyl]acetyl]amino]-3-methyl-8-oxo-3-thia-1-azabicyclo[4.2.0]oct-2-ene-2-carboxylic acid The title compound is obtained in quantitative yield as described in Procedure VII from 7-[[[[(tert-butyloxycarbonylamino)-[4-hydroxy-3-(1-methyl-1$\underline{H}$-tetrazol-5-yl)-thio]methyl]phenyl]acetyl]amino]-3-methyl-8-oxo-5-thia-1-azabicyclo[4.2.0]oct-2-ene-2-carboxylic acid tert-butyl ester.

NMR (DMSO-$D_6$) ppm ($\delta$) 2.0 (s,3), 3.4 (m,2), 3.8 (s,3), 4.4 (s,2), 4.8–5.0 (m,2), 5.6 (m,1), 6.6–7.5 (m,3).

EXAMPLE 63

7-[[Amino[4-hydroxy-3-[(methylsulfinyl)methyl]phenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid trifluoroacetate The title compound is obtained in quantitative yield as described in Procedure VII from 7-[[(tert-butyloxycarbonylamino)-[4-hydroxy-3-[(methylsulfinyl)methyl]phenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid.

NMR (DMSO-$D_6$) ppm ($\delta$) 2.4 (s,3), 2.6 (s,3), 3.4 (m,2), 3.9 (s,2), 4.2 (m,2), 4.8 (m,2), 5.4 (m,1), 6.6–7.5 (m,3).

EXAMPLE 64

7-[[Amino[4-hydroxy-3-[(methylsulfonyl)methyl]phenyl]acetyl]amino]-3-[[(1-methyl-1$\underline{H}$-tetrazo-5-yl)thio]methyl]-8-oxo-5-thia-1-azabicyclo[4.2.0]oct-2-ene-2-carboxylic acid trifluoroacetate The title compound is obtained in quantitative yield as described in Procedure VII from 7-[[(tert-butyloxycarbonylamino)-[[4-hydroxy-3-(methylsulfonyl)methyl]phenyl]acetyl]amino]-3-[[(1-methyl-1$\underline{H}$-tetrazol-5-yl)thio]methyl]-8-oxo-5-thia-1-azabicyclo[4.2.0]oct-2-ene-2-carboxylic acid.

NMR (TFA-D) ppm ($\delta$) 3.12 (s,3), 3.55 (m,2), 3.9 (s,3), 4.5 (m,2), 5.1 (d,1), 5.3 (s,1), 5.7 (d,1), 6.9–7.5 (m,3).

EXAMPLE 65

7-[[[3-Azido-4-hydroxyphenyl]acetyl]amino]-7-methoxy-3-[[(5-methyl-1,3,4-thiadiazol-2-yl)thio]methyl]-8-oxo-5-thia-1-azabicyclo[4.2.0]oct-2-ene-2-carboxylic acid The title compound is prepared when 3-azido-4-hydroxybenzeneacetic acid is reacted with 7-amino-7-methoxy-3-[[(5-methyl-1,3,4-thiadiazol-2-yl)thio]methyl]-8-oxo-5-thia-1-azabicyclo[4.2.0]oct-2-ene-2-carboxylic acid according to Procedure V.

EXAMPLE 66

7-[[Amino[3-(chloromethyl)-4-hydroxyphenyl]acetyl]amino]-3-methyl-8-oxo-5-thia-1-azabicyclo[4.2.0]-oct-2-ene-2-carboxylic acid A solution of 0.05 mole of $\alpha$-amino-3-(chloromethyl)-4-hydroxybenzeneacetic acid in methylene chloride at 15° C. is treated with hydrogen chloride gas to form the amine hydrochloride salt. Thionyl chloride, about 0.06 mole, is added and the mixture stirred for 3 hours. The acid chloride hydrochloride is recovered by filtration.

The thus formed acid chloride, hydrochloride, 0.03 mole, is added to tetrahydrofuran which contains 0.03 mole of 7-amino-3-methyl-8-oxo-5-thia-1-azabicyclo[4.2.0]oct-2-ene-2-carboxylic acid and 0.03 mole of N,N-dimethylaniline. The temperature is maintained at 15° C. and the mixture is stilled for 2 hours. The solvent is removed under vacuum and the residue is extracted with ethyl acetate. The ethyl acetate is dried over magnesium sulfate, filtered and evaporated to give the title compound.

EXAMPLE 67

7-[[Carboethoxy[4-hydroxy-3-(methoxymethyl)phenyl]acetyl]amino]-3-methyl-8-oxo-5-thia-1-azabicyclo[4.2.0]oct-2-ene-2-carboxylic acid $\alpha$-Carboxy-4-hydroxy-3-(methoxymethyl)benzeneacetic acid, 0.15 mole, in ethyl ether is reached with 0.16 mole of thionyl chloride in the presence of 1 drop of dimethylformamide. This mixture is refluxed for 3 hours. About 0.2 mole of ethanol is added and the material refluxed for about 1 hour. The solvents are removed and $\alpha$-carboethoxy-4-hydroxy-3-(methoxymethyl)benzeneacetic acid is recovered. This thus formed compound is then reacted with 7-amino-3-methyl-8-oxo-5-thia-1-azabicyclo[4.2.0]oct-2-ene-2-carboxylic acid according to Procedure VI to give the title compound.

EXAMPLE 68

7-[[[3-Azido-$\alpha$,4-(dihydroxyphenyl)]acetyl]amino]-3-methyl-8-oxo-5-thia-1-azabicyclo[4.2.0]oct-2-ene-2-carboxylic acid A slight excess of bis-(trimethylsilyl)acetamide (about 0.21 mole) in THF is reacted with 0.20 mole of 3-azido-$\alpha$,4-dihydroxybenzeneacetic acid in THF containing about 0.20 mole of triethylamine. This mixture is refluxed for about 30 minutes.

The thus protected hydroxy compound is then reacted with 7-amino-3-methyl-8-oxo-5-thia-1-azabicyclo[4.2.0]-oct-2-ene-2-carboxylic acid according to Procedure V to give the title compound.

EXAMPLE 69

7-[[[3-[(methylthio)methyl]-4-(hydroxy)phenyl]sulfoacetyl]amino]-3-[[(1-methyl-1H-tetrazol-5-yl)thio]methyl]-8-oxo-5-thia-1-azabicyclo[4.2.0]oct-2-ene-2-carboxylic acid The title compound is prepared when α-sulfo[3-[(methylthio)methyl]-4-hydroxy]-benzeneacetic acid is reacted with 7-amino-3-[[(1-methyl-1H-tetrazol-5-yl)thio]methyl]-8-oxo-5-thia-1-azabicyclo[4.2.0]oct-2-ene-2-carboxylic acid according to Procedure VI.

EXAMPLE 70

7-[[(tert-Butyloxycarbonyl)amino[4-hydroxy-3-(methoxymethyl]phenyl)acetyl]amino]-7-methoxy-3-methyl-8-oxo-5-thia-1-azabicyclo[4.2.0]oct-2-ene-2-carboxylic acid The title compound is prepared by reacting α-(tert-butyloxycarbonyl)amino-3-(methoxymethyl)-4-hydroxybenzeneacetic acid with 7-amino-7-methoxy-3-methyl-8-oxo-5-thia-1-azabicyclo[4.2.0]oct-2-ene-2-carboxylic acid according to Procedure V.

The thus formed compound may be reacted with trifluoroacetic acid for 15 minutes according to Procedure VII to give 7-[[(amino[4-hydroxy-3-(methoxymethyl)phenyl]acetyl]amino]-7-methoxy-3-methyl-8-oxo-5-thia-1-azabicyclo[4.2.0]oct-2-ene-2-carboxylic acid.

EXAMPLE 71

7-[[Amino[3-(azidomethyl)-4-hydroxyphenyl]acetyl]amino]-3-[[(5-methyl-1,3,4-thiadiazol-2-yl)thio]methyl]-8-oxo-5-thia-1-azabicyclo[4.2.0]oct-2-ene-2-carboxylic acid This procedure is based on the general procedure described in *J. Antibiotics*, 23, 131 (1970). About 0.03 mole of 3-(acetyloxy)methyl-7-[[amino[3-(azidomethyl)-4-hydroxyphenyl]acetyl]amino]-8-oxo-5-thia-1-azabicyclo-[4.2.0]oct-2-ene-2-carboxylic acid, about 0.03 mole of sodium bicarbonate and about 0.03 mole of 5-methyl-1,3,4-thiadiazol-2-ylthiol are placed in 200 ml of a phosphate buffer of a pH of 5.6. This mixture is heated at about 60° C. for about 6 hours. At the end of this time the pH is adjusted to 3–4 by the addition of hydrochloric acid. The aqueous phase is extracted with ethyl acetate. The ethyl acetate extract is washed with sodium chloride and dried over magnesium sulfate. Removal of the magnesium sulfate and evaporation of the ethyl acetate gives the title compound.

EXAMPLE 72

7-[[Amino[3-(azidomethyl)-4-hydroxyphenyl]acetyl]amino]-3-methyl-8-oxo-5-thia-1-azabicyclo[4.2.0]oct-2-ene-2-carboxylic acid 7-[[Amino[3-(chloromethyl)-4-hydroxyphenyl]acetyl]amino]-3-methyl-8-oxo-5-thia-1-azabicyclo[4.2.0]oct-2-ene-2-carboxylic acid (0.02 mole) is added to tetrahydrofuran at about 40° C. Sodium azide (0.04 mole) in tetrahydrofuran is added and the resulting mixture is stirred for 3 hours. The tetrahydrofuran is evaporated and the residue is treated with water to remove the sodium chloride and the excess sodium azide. The resulting residue is taken up in ethyl acetate and the ethyl acetate is dried over magnesium sulfate. Filtration removes the magnesium sulfate and removal of the ethyl acetate gives the title compound.

In like manner and using equivalent amounts of sodium methoxide, sodium methylthiolate and potassium cyanide and sodium bisulfite in place of sodium azide gives respectively
7-[[amino[4-hydroxy-3-(methoxymethyl)phenyl]acetyl]amino]-3-methyl-8-oxo-5-thia-1-azabicyclo[4.2.-0]oct-2-ene-2-carboxylic acid;
7-[[amino[4-hydroxy-3-(methylthiomethyl)phenyl]acetyl]amino]-3-methyl-8-oxo-5-thia-1-azabicyclo[4.2.0]oct-2-ene-2-carboxylic acid;
7-[[amino[3-(cyanomethyl)-4-hydroxyphenyl]acetyl]amino]-3-methyl-8-oxo-5-thia-1-azabicyclo[4.2.0]oct-2-ene-2-carboxylic acid; and
7-[[amino[4-hydroxy-3-(sulfomethyl)phenyl]acetyl]amino]-3-methyl-8-oxo-5-thia-1-azabicyclo[4.2.-0]oct-2-ene-2-carboxylic acid.

EXAMPLE 73

7-[[Amino[[[(aminoiminomethyl)thio]methyl]-4-hydroxyphenyl]acetyl]amino]-3-methyl-8-oxo-5-thia-1-azabicyclo[4.2.0]oct-2-ene-2-carboxylic acid dihydrochloride 7-[[Amino[3-(chloromethyl)-4-hydroxyphenyl]acetyl]amino]-3-methyl-8-oxo-5-thia-1-azabicyclo[4.2.-0]oct-2-ene-2-carboxylic acid (0.02 mole) is added to tetrahydrofuran-water (2:1) maintained at 40° C. Isothiourea (0.02 mole) is dissolved in water and added to the above formed solution. This mixture is stirred for 4 hours and the solvents are removed. The title compound is recovered as the dihydrochloride.

EXAMPLE 74

7-[[Amino[4-hydroxy-3-(methoxymethyl)phenyl]acetyl]amino]-7-methoxy-3-methyl-8-oxo-5-thia-1-azabicyclo[4.2.0]oct-2-ene-2-carboxylic acid, 2-amino-3-methyl-butyryloxymethyl ester A suspension of 5 grams of 7-[[amino[4-hydroxy-3-(methoxymethyl)phenyl]acetyl]amino]-7-methoxy-3-methyl-8-oxo-5-thia-1-azabicyclo[4.2.0]oct-2-ene-2-carboxylic acid, sodium salt and 8.5 grams of N-tert-butoxycarbonyl-L-valine chloromethyl ester, which is prepared by the general procedure described in W. German Offen. No. 2,236,620, are mixed in 100 ml of dimethylformamide and stirred for 72 hours. The mixture is diluted with ethyl acetate, washed with water and aqueous bicarbonate and again with water. The ethyl acetate portion is dried over magnesium sulfate, filtered and evaporated to give 7-[[amino[4-hydroxy-3-(methoxymethyl)phenyl]acetyl]amino]-7-methoxy-3-methyl-8-oxo-5-thia-1-azabicyclo[4.2.0]oct-2-ene-2-carboxylic acid, N-tert-butoxycarbonyl-2-amino-3-methyl-butyryloxymethyl ester from which the protecting group can be removed by standard procedures to give the title compound.

EXAMPLE 75

7-[[Amino[3-(azidomethyl)-4hydroxyphenyl]acetyl]amino]-3-methyl-8-oxo-5-thia-1-azabicyclo[4.2.0]oct-2-ene-2-carboxylic acid pivaloyloxymethyl ester The sodium salt of 7-[[amino[3-(azidomethyl)-4-hydroxyphenyl]acetyl]amino]-3-methyl-8-oxo-5-thia-1-azabicyclo[4.2.0-oct-2-ene-2-carboxylic acid is added to 40 ml of dry dimethylformamide (DMF) and stirred for about 30 minutes. Then 4.0 ml of chloromethylpivalate in 5 ml of DMF is added. This mixture is stirred for 4 hours at room temperature. The mixture is diluted with ethyl acetate and thoroughly washed with water. The ethyl acetate portion is dried over sodium sulfate, filtered and evaporated to give the title compound.

EXAMPLE 76

7-[[[4-Hydroxy-3-(methylthiomethyl)phenyl]acetyl-]amino]-3-methyl-8-oxo-5-thia-1-azabicyclo[4.2.0]oct-2-ene-2-carboxylic acid, p-pivaloyloxybenzyl ester 7-[[[4-Hydroxy-3-(methylthiomethyl)phenyl]acetyl-]amino]-3-methyl-8-oxo-5-thia-1-azabicyclo[4.2.0]oct-2-ene-2-carboxylic acid, sodium salt, 6.0 mmole, is added to 35 ml of dimethylformamide (DMF) with stirring. Then about 2 equivalents of pivaloyloxybenzyl alcohol is added to the mixture cooled to 0° C. Then 7.0 mmole of dicyclohexylcarbodiimide in 7.5 ml of DMF is added to the mixture which is stirred at 0° C. for 1 hour and at room temperature for 4 hours. The reaction mixture is diluted with ethyl acetate, washed thoroughly with water and the organic phase is dried and filtered. Removal of the ethyl acetate gives the title compound.

EXAMPLE 77

7-[[[α,4-Dihydroxy-3-(methoxymethyl)phenyl]acetyl-]amino]-3-methyl-8-oxo-5-thia-1-azabicyclo[4.2.0]oct-2-ene-2-carboxylic acid N-ethoxycarbonyl-N-methylaminomethyl ester The sodium salt of 7-[[[α,4-dihydroxy-3-(methoxymethyl)phenyl]acetyl]amino]-3-methyl-8-oxo-5-thia-1-azabicyclo[4.2.0]oct-2-ene-2-carboxylic acid, 2.5 mmole, in 50 ml of dimethylformamide is treated at room temperature with 2.5 mmole of N-chloromethyl-N-methylurethane for 1 hour. The mixture is poured into ice water and the precipitated solid is removed by filtration and washed with water. The solid is dissolved in ethyl acetate, washed with aqueous sodium bicarbonate and then with water. The organic layer is dried over magnesium sulfate, filtered and evaporated to give the title compound.

We claim:
1. A compound of the formula

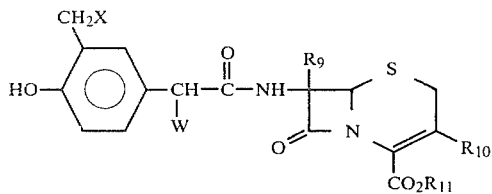

wherein W is hydrogen, —SO₃H or —NHR₂, wherein R₂ is hydrogen, tert-butyloxycarbonyl or

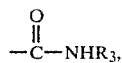

wherein R₃ is hydrogen, a lower alkyl group of from 1 to 4 carbon atoms or a phenyl group; X is chloro, bromo, an alkoxy group from 1 to 4 carbon atoms; an R₄—S—;

R₄SO₂— group wherein R₄ is a lower alkyl group of from 1 to 4 carbon atoms; azido; cyano; NCNH—; HSO₃—; —SCN; —OCN; CH₃SO₂NH—; isothiourea; mono-substituted isothiourea wherein the substituents are amino, formylamino, guanylamino, a lower alkyl group of from 1 to 4 carbon atoms and concatenated alkylene groups in the form of a series of from 2 to 6 methylene groups; pyridylthio; 1-methyltetrazol-5-ylthio; 1,3,4-thiadiazol-2-ylthio; 1,3,4-triazol-2-ylthio; —SH; SSO₃H; F₃CS—;

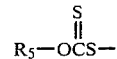

wherein R₅ is lower alkyl of from 1 to 4 carbon atoms;

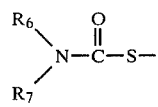

wherein R₆ and R₇ separately are hydrogen, a lower alkyl group of from 1 to 4 carbon atoms, when taken together R₆ and R₇ may form a concatenated chain of from 4 to 7 methylene groups, a concatenated chain of from 5 to 7 methylene groups wherein one of these methylene groups is replaced by an oxygen atom or an R₈—N group wherein R₈ is a lower alkyl group of from 1 to 4 carbon atoms with the proviso that when X is chlorine or bromine R₂ is other than tert-butyloxycarbonyl; R₉ is hydrogen or methoxy; R₁₀ is methyl or acetyloxymethyl; R₁₁ is hydrogen, a straight or branched lower alkyl group of from 1 to 4 carbon atoms, a straight or branched alkanoyloxymethyl group in which the alkanoyl moiety has from 1 to 4 carbon atoms; and is straight or branched, an alkanoylaminomethyl group in which the alkanoyl moiety is straight or branched and has from 1 to 4 carbon atoms and the amine nitrogen may be substituted with a straight or branched lower alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched lower alkyl group of from 1 to 4 carbon atoms, p-(alkanoyloxy)-benzyl group in which the alkanoyl moiety is straight or branched and has from 1 to 4 carbon atoms; an aminoalkanoyloxymethyl group in which the alkanoyl moiety has from 2 to 15 carbon atoms and the amine nitrogen may be mono- or di-substituted with a straight or branched lower alkyl group having from 1 to 4 carbon atoms; and pharmaceutically acceptable salts thereof.

2. A compound of claim 1 wherein X is other than bromine or chlorine, W is —NHR₂ wherein R₂ is tert-butyloxycarbonyl and R₁₀ is methyl.

3. A compound of claim 1 wherein W is —NHR₂ wherein R₂ is hydrogen and R₁₀ is methyl.

4. A compound of claim 1 which is 7-[[amino[4-hydroxy-3-(methoxymethyl)phenyl]acetyl]amino]-3-methyl-8-oxo-5-thia-1-azabicyclo[4.2.0]oct-2-ene-2-carboxylic acid or a pharmaceutically acceptable salt thereof.

5. A compound of claim 1 which is 7-[[amino[3-(azidomethyl)-4-hydroxyphenyl]acetyl]amino]-3-methyl-8-oxo-5-thia-1-azabicyclo[4.2.0]oct-2-ene-2-carboxylic acid or a pharmaceutically acceptable salt thereof.

6. A compound of claim 1 which is 7-[[amino[4-hydroxy-3-(methylthiomethyl)phenyl]acetyl]amino]-3- methyl-8-oxo-5-thia-1-azabicyclo[4.2.0]oct-2-ene-2-carboxylic acid or a pharmaceutically acceptable salt thereof.

7. A compound of claim 1 which is 7-[[[[amino[4-hydroxy-3-(1-methyl-1H-tetrazol-5-yl)thio]methyl]-phenyl]acetyl]amino]-3-methyl-8-oxo-3-thia-1-azabicyclo[4.2.0]oct-2-ene-2-carboxylic acid or a pharmaceutically acceptable salt thereof.

* * * * *